US012675001B2

(12) United States Patent
Wu et al.

(10) Patent No.: US 12,675,001 B2
(45) Date of Patent: Jul. 7, 2026

(54) CORRECTIVE LENS APPARATUS AND METHOD

(71) Applicants: Tien-Shu Wu, Del Mar, CA (US);
Yen-Ting Wu, Del Mar, CA (US);
Alejandro A. Goebel-Quintana, Del
Mar, CA (US); Donn K. Harms, Del
Mar, CA (US); Patrick Hussey, Del
Mar, CA (US)

(72) Inventors: Tien-Shu Wu, Del Mar, CA (US);
Yen-Ting Wu, Del Mar, CA (US);
Alejandro A. Goebel-Quintana, Del
Mar, CA (US); Donn K. Harms, Del
Mar, CA (US); Patrick Hussey, Del
Mar, CA (US)

( * ) Notice: Subject to any disclaimer, the term of this
patent is extended or adjusted under 35
U.S.C. 154(b) by 332 days.

(21) Appl. No.: 18/228,611

(22) Filed: Jul. 31, 2023

(65) Prior Publication Data

US 2023/0375855 A1     Nov. 23, 2023

Related U.S. Application Data

(63) Continuation-in-part of application No. 16/853,259,
filed on Apr. 20, 2020, now Pat. No. 11,714,297,
which is a continuation of application No.
15/754,506, filed as application No.
PCT/US2016/049110 on Aug. 26, 2016, now Pat. No.
10,627,648.

(60) Provisional application No. 63/465,945, filed on May
12, 2023, provisional application No. 62/210,024,
filed on Aug. 26, 2015.

(51) Int. Cl.
*G02C 7/02* (2006.01)
*G02C 1/00* (2006.01)
*G02C 1/06* (2006.01)
*G02C 7/08* (2006.01)
*G02C 7/16* (2006.01)
*A61F 9/02* (2006.01)

(52) U.S. Cl.
CPC ................. *G02C 7/02* (2013.01); *G02C 1/00*
(2013.01); *G02C 1/06* (2013.01); *G02C 7/086*
(2013.01); *G02C 7/16* (2013.01); *A61F*
*2009/021* (2013.01)

(58) Field of Classification Search
CPC . G02C 7/02; G02C 7/086; G02C 7/16; G02C
7/10; G02C 7/12; G02C 1/00; G02C
1/06; A61F 2009/021
USPC .......................................................... 351/83
See application file for complete search history.

(56) References Cited

U.S. PATENT DOCUMENTS

| | | | | | |
|---|---|---|---|---|---|
| 5,748,279 | A * | 5/1998 | Glanzbergh | ............. | G02C 9/00 351/45 |
| 6,290,354 | B1 * | 9/2001 | Safran | ...................... | G02C 9/00 351/84 |
| 6,502,937 | B2 * | 1/2003 | Yang | ........................ | G02C 9/00 351/57 |
| 7,055,951 | B2 * | 6/2006 | Canavan | ................ | G02C 11/08 351/57 |

(Continued)

*Primary Examiner* — William R Alexander

(74) *Attorney, Agent, or Firm* — Donn K. Harms

(57) ABSTRACT

A unitary lens structure is provided which is employable
with spectacles as well as goggles and safety eyewear and
AR and VR eyewear. The lens is formed as a unitary
structure with a curved first lens having one or a plurality of
projections thereon having surfaces which are formable to
prescription eyewear providing vertical vision correction
and curved horizontal vision correction.

12 Claims, 15 Drawing Sheets

(56)                    References Cited

U.S. PATENT DOCUMENTS

| | | | |
|---|---|---|---|
| 7,204,589 B2 * | 4/2007 | Pieterman ................ | G02C 9/00 |
| | | | 351/48 |
| 7,866,812 B1 * | 1/2011 | Tullis ....................... | G02C 9/04 |
| | | | 2/441 |
| 10,901,167 B1 * | 1/2021 | Courter, Jr. ......... | B29C 45/0025 |
| 11,714,297 B2 * | 8/2023 | Quintana ................ | G02C 1/00 |
| | | | 351/83 |
| 2007/0279577 A1 * | 12/2007 | Stanley ................. | G02C 11/08 |
| | | | 351/62 |
| 2011/0134388 A1 * | 6/2011 | Hsu .......................... | G02C 7/06 |
| | | | 351/159.48 |
| 2012/0127425 A1 * | 5/2012 | Goebel Quintana ........................ | |
| | | | B29D 11/00009 |
| | | | 351/159.01 |
| 2015/0253574 A1 * | 9/2015 | Thurber ............ | G02B 27/0172 |
| | | | 359/630 |
| 2019/0151152 A1 * | 5/2019 | Goebel Quintana .... | G02C 7/10 |

* cited by examiner

CORRECTIVE LENS APPARATUS AND METHOD

This application claims priority to U.S. Provisional Patent Application 63/465,945 filed on May 12, 2023, and is a Continuation in Part application to U.S. patent application Ser. No. 16/853,259 filed on Apr. 20, 2020, which is a Continuation of U.S. patent application Ser. No. 15/754,506 filed on Feb. 22, 2018, which was a national filing of PCT/US16/49110 filed on Aug. 26, 2016, which claims priority to U.S. Provisional Patent Application Ser. No. 62/210,024 filed on Aug. 26, 2015, all of which are incorporated in their respective entirety by this reference thereto.

BACKGROUND OF THE INVENTION

1. Field of the Invention

The present invention relates generally to corrective lenses employed in eyewear such as eyeglasses, protective eyewear, and goggles. More particularly, the disclosed system and method relates to a lens having a first portion forming a shield or surrounding portion formed of optically correct material and having one or a plurality of projections permanently positioned thereon for formation of corrective lenses. So configured, the device forms a unitary structure where the perimeter of the first portion of the lens is adapted for engagement in an eyewear frame or goggle or other lens frames.

2. Prior Art

Individuals with eyesight problems have turned to corrective eyewear for hundreds of years. As a general rule, such eyesight problems are a result of the physical characteristics of the eye of the person requiring corrective lenses. Over the duration such corrective lenses have been provided to users requiring them. The basic nature of grinding lenses to refocus the image captured by the eye of the user onto the receptive rear surface of their eye in a manner rendering clearer vision has progressed to provide corrections for issues other than near or far sightedness. However, the basic premise of positioning a lens in front of the eye of the user to refocus incoming light is still present today.

In some instances the nature of construction of corrective lenses, especially in combination with safety or protective eyewear, has been less than adequate. For example, users of corrective lenses who suffer from severe farsightedness require very thick lenses to correct their vision, which are not well adapted for use in combination with a shield type eyewear such as goggles. Further, such thick lenses have perimeters which limit the engagement to eyeglass frames.

Further, those with nearsightedness or farsightedness or who suffer from other vision acuity problems also have problems trying to wear protective goggles such as military members who wear goggles, or others who wear sport goggles for activities such as skiing or motorcycling. The problem of corrective lenses is also an issue when combined with workers who must wear safety goggles.

Conventionally, such users have been forced to try and fit their eyeglasses within the cavity of the goggle or safety goggle covering their eyes. In such a combination, the user must view their surroundings through both the goggle lens, and their own lenses positioned in-between the goggle lens and their face. Such has led to poor vison from fogging, glare from the interaction of spaced refraction surfaces, shadow images caused by the spaced lenses, and other issues caused by the interaction between the eyeglass lenses spaced from the goggle lens or lenses.

In prior art, a partial solution to the problem has been advanced. For example, U.S. Pat. No. 8,814,349 (Quintana), while a leap forward in the concept of providing a unitary structure of two corrective lenses and a shielding lens, it does not provide panoramic vision correction to the user which would eliminate the need to turn their head to see clearly. Quintana, while teaching the novel concept of using two planar projecting portions rising from one side of a first curving or panoramic lens for formation of ophthalmic lenses, it makes no accommodation for the risk of cracking along the perimeter of the projecting portions at their intersection with the front curving lens. Additionally, refraction of light through the sidewall of the projecting portions and adjacent their intersection with the front panoramic lens, as taught by the Quintana reference, may generate refractive qualities, such as colorized light, which has been found to be distracting to users. Additionally, when employed for goggles which form a sealed cavity in front of the face of the user, the dissimilar thicknesses of the panoramic lens or shield areas thereof with projecting portions can have thermal issues during formation due to the retention of heat in the thicker areas. Additionally, no prior art teaches a manner in which smaller projections on a curved panoramic shield can be ground to required characteristics to provide vision correction to a wearer.

As such, there exists an unmet need for a corrective lens which curves around the eye of the wearer which is formable upon a surface of a thinner panoramic lens. Such a lens should provide an intersection of the perimeter of the curved projecting material from which the ophthalmic lens is formed and the planar panoramic front lens is configured to prevent cracking and stress fractures over time and temperature differentials. Such a device should provide a form which is employable in single lenses of eyewear as well as in dual lens configurations of protective eyewear shields and sport and protective goggle devices and in shapes which allow for formation of progressive lenses in both the horizontal and vertical direction. Still further, such a device and method should provide projections on the frontal panoramic lens which are machinable to corrective lenses using conventional lens grinding machinery, in spite of the large and highly curved panoramic lens surrounding the projecting portions.

The forgoing examples of related art and limitations related therewith are intended to be illustrative and not exclusive, and they do not imply any limitations on the invention described and claimed herein. Various limitations of the related prior art will become apparent to those skilled in the art upon a reading and understanding of the specification below and the accompanying drawings.

OBJECTS OF THE INVENTION

It is an object of this invention to provide a unitary structure of a first curved or panoramic lens having one or a plurality of curved projecting portions formed thereon which may be cut to form curved ophthalmic lenses.

It is a further object of this invention to provide such a unitary structure where the first lens on which the projecting portion is formed, surrounds the projecting portion in a thinner cross section of optical material which may be fit to frames heretofore precluded for users with thick lens prescriptions.

It is a further object of this invention to eliminate or at least minimize the potential for cracking of the thinner front or panoramic lens at the intersection of the perimeter side-walls of the projecting portions and the panoramic lens they are formed upon.

It is a further object of this invention to provide the projecting portions formed upon a surface of a larger curved lens to be machinable using conventional lens grinding machinery despite the large and curved first lens portions surrounding them.

It is also an object of this invention to provide the projecting portions formed in unitary structure with the surrounding panoramic first lens in shapes which may be cut to allow for progressive vision correcting lenses in both the horizontal and vertical directions.

It is yet a further object of this invention to provide a combination panoramic first lens having one or a plurality of curving projection portions which, when formed to a pre-scription correction required for a user, allows the user to see clearly to the sides of their head without the need to turn their head.

Another object of this invention is the provision of such a panoramic front lens with one or a plurality of curving projecting portions on a side facing the face of the user which may be formed to the sight prescription needs of the user and positioned into an AR or VR headset or in com-bination with AR or VR eyeglasses.

These and other objects, features, and advantages of the present lens invention and system herein, as well as the advantages thereof over existing prior art, which will become apparent from the description to follow, are accom-plished by the improvements described in this specification and hereinafter described in the following detailed descrip-tion which fully discloses the invention, but should not be considered as placing limitations thereon.

SUMMARY OF THE INVENTION

The present invention is a lens formed into a unitary structure featuring a first lens portion formed in a generally concave panoramic shape and having one or a plurality of projecting portions on a rear surface, defined in shape by a perimeter edge thereof, rising from a permanent connection with a first surface of the first lens portion. This curved or panoramic first lens portion is in a unitary structure with one or a plurality of projecting portions extending from a rear surface thereof which are formable to provide curving vision correction to both of the eyes of a wearer or user. The formed first lens portion with the projection or projections, formed to correct the vision of both eyes of a user, is operatively engageable within an AR or VR headset. Alternatively, the formed first lens and projection combination may be formed in an engagement with the display screen of such headsets to provide users requiring glasses, which will not fit within the headset, vision correction forward and to the sides by simply moving their eyes rather than their head.

The cross sectional thickness of the first lens portion, which curves around and surrounds the projecting portions, is thinner than the cross sectional thickness of the area within the bounds of the perimeter of the projecting portions rising from an inner or first side of the first lens portion.

In a preferred mode of the device, the radii of the first lens portion or shield can vary slightly to better accommodate the portion in a central area of the shield where the projections are located and reduce distortion further. For example, the first lens portion or shield can have a general radii of a front surface of the shield or first lens portion, which is 75 mm. However, the central area where the projections extend can be 65 mm (flatter). This slight flattening of the arc in the central portion has been found to increase the range of possible corrective prescriptions to be produced. However, the difference in radii would not be noticeable to the naked eye, and the first portion or shield will maintain, in general, its original shape for cosmetics and fitment to conventional frames and goggle housings.

This curved or panoramic first lens portion is optically correct across its entire surface such that the thinner sur-rounding area, on both sides of the central portion, is optically correct and significantly thinner in cross section to allow engagement within an eyeglass frame or goggle or AR or VR headset, but still adapted for an engagement to temple portions to form a shield.

In all modes of the lens device herein disclosed, it is preferred that the one or plurality of projections extending from the side of the panoramic curved first lens portion curve around from a first side adjacent a central area positioned in front of the nose of the user to a second side adjacent one side of the first lens portion to allow for formation of each projection to yield a corrective lens for the user.

In all modes of the lens device herein disclosed, it is preferred that the one or plurality of projections extending from the user-face side of the curved first lens portion provide panoramic vision correction wherein the wearer has correct vision when turning their eyes and thereby eliminat-ing the need to turn their entire head to see clearly.

In some or all modes of the device herein, the intersection of the perimeter edge of the sidewall, defining the shape of the projecting portion employed for lens formation, with the first surface for the first lens portion is preferably neither a perpendicular intersection of two planar surfaces nor an intersection of a straight line extending up the sidewall surface of the projecting portion.

In some or all modes of the device herein, that intersection of the sidewall of the perimeter of the projecting portions which defines a shape of the projecting portions is preferably formed such that the line running up the sidewall surface from the intersection with the first surface of the first lens portion is non linear in that a portion of the sidewall changes direction relative to the rest of the sidewall extending to the edge of the machinable surface of the projecting portion.

In all modes of the device herein, one or, more preferably, a plurality of such projecting portions are engaged with the surrounding optically correct panoramic lens in a manner to yield a permanent connection between the two, which forms a unitary structure with minimal, if any, optical distortion therethrough. This connection between the projecting por-tion or portions is preferably achieved by molded formation of a unitary structure of the projecting portions and the first lens portion or shield defining a panoramic lens.

In forming a unitary structure, the projections and first lens portion or shield can be molding as a single unit, or the projections may be co-molded into the first lens portion to form a unitary structure. In co-molding, the projections are pre-formed and subsequently communicated into the mold for the first lens portion, wherein a first surface of the projections melts and joins to the projecting portions to form a unitary structure.

As noted, it is preferable that the intersection of the perimeter sidewall of the projections, and the central portion of the first lens portion, is not perpendicular. Thus, in molding or forming the unitary structure of the first lens portion and projections, this intersection is preferably formed curved or angled. It is also preferred that a width of the intersection of the angled or curved surface forming the connection be small and not rise more than a millimeter above the surface of the first lens portion, because experimentation has shown this to minimize any distortion or light refraction issues.

In all modes of the lens device herein, the projections formed in the unitary structure with the first lens portion preferably curve around the eyes of the user from a central area of the first lens portion to a position adjacent the side edge of the panoramic first lens portion. This curved configuration allows the projection or projections to be formed to ophthalmic lens portions to correct the vision of the wearer or user. Once formed to correct the vision of the user, the curved projection or projections yield concurrent horizontal vision correction curving to the sides of the panoramic first lens portion as well as vertical progressive vision correction.

As noted, this curved projection or projections, once formed to correct the vision or the user, provides corrected vision to both sides of the head of the user which is achieved when simply turning their eyes to the side. It eliminates the need for users to turn their head to see clearly as is required with conventional eyeglasses. This corrective function is especially preferred during sports, such as bicycling, where head turning is not desirable and where users are wearing AR or VR headsets and head turning to yield corrected vision would be useless.

The depicted shape or shapes of the projecting portions which is defined by the sidewall intersecting the first surface of the first lens portion, can be formed, as shown herein, or in other shapes, which will allow for cutting or forming of panoramic vision correcting lenses in combination with vertically corrective progressive lenses. For example, one such shape, as shown in the figures, has a wider diameter adjacent the two side edges or ends of the panoramically curved first lens portion which narrows toward the middle area of the first curved lens.

This preferred shape allows for portions of the projecting portion or portions to extend closer to the bridge of the nose, while concurrently extending to the temple and well below the nose. This extended rectangular shape with a curve extending from a nose-side to the lower edge allows for formation of progressive lenses which are highly customized to a user where the provided vision correction is both from top to bottom and sideways from nose to temple. Such provides corrective vision to the user who may keep their head facing forward and simply turn their eyes to see clearly to both sides which is important where the user is wearing AR or VR headwear and needs vision correction therefor.

Additionally, if formed of a curved first lens portion or shield with one or a plurality of projecting portions thereon for engagement to goggles or an eyeglass frame, a polarizing layer may be placed in-between the material forming the first lens portion and the projecting portion which is machinable to form the corrective lens. This will provide polarized light transmission to the wearer. Such may be accomplished by layering the first lens portion.

Still further, the shape of the projecting portion defined by the sidewall intersecting the first surface of the first lens portion can be formed in shapes, as shown herein, or other shapes, which will allow for cutting of progressive lenses therein for the user providing vertical and horizontal vision correction without the need for the user to turn their head to see clearly. For example, one such shape, as shown in the figures, has a wider diameter adjacent the two ends of the curved first lens portion and narrows and extends toward the middle.

This preferred shape allows for portions of the projecting portion to extend closer to the bridge of the nose, while concurrently extending toward the temple of the user and well below the nose. This extended rectangular shape with a curve extending from a nose-side to the lower edge allows for formation of vertical and horizontal progressive vision correcting lenses which are highly customized to a user where the progressive lens can be both horizontal from top to bottom and sideways from nose to temple. Since the surrounding section of the first lens portion is significantly thinner than the unitary portion of the projecting portion and first lens portion, the formed lens or shield can be configured for users.

Additionally shown is a preferred removable tooling engagement member which may be formed as part of the unitary lens. By formation of this tooling engagement member, in a break away or removable engagement extending perpendicular from the axis of the unitary lens and in a centered position, it allows for machining of the raised surfaces of the projecting portions to form corrective lenses by an engagement of the unitary structure to a lens machining apparatus using the removable projecting member. As noted, this tooling engagement, and the unitary structure of the first lens and projecting portion, overcomes the problems associated with the prior art, where the large curved panoramic first lens portion blocks engagement in a conventional fashion to lens grinding machines. Once the projecting portion surface or surfaces have been properly machined to the corrective lens, the projecting member can be removed by breaking a frangible portion or cutting it from the side edge.

Still further, the unitary lens herein is especially well adapted to the formation of protective eyewear, as well as for sport goggles and the like. This is because the one or plurality of raised portions are permanently engaged and extend from the first surface of the first lens portion surrounding the raised portions, and the first lens portion is large and panoramic and has thin edges, the unitary structure provides a goggle which is protected from fogging and the like.

Further, as noted above, a wafer or layer of polarizing film may be positioned between the lenses, or within the pre formed projecting portions which are later co-molded to the first lens portion, thereby providing polarized eyewear to the user for high glare conditions.

In all modes, both the first lens portion surrounding the engaged projecting portion, and the projecting portion or portions, may be formed of polycarbonate plastic or other optically suitable polymeric or plastic materials, such as a monomer plastic, or a "High Index" plastic.

With respect to the above description, before explaining at least one preferred embodiment of the panoramic vision correcting lens for use in combination with eyeglass or sunglass frames or an AR or VR type headwear in detail, it is to be understood that the invention is not limited in its application to the details of construction and to the arrangement of the steps in the following description or illustrated in the drawings. The unitary lens invention herein described is capable of other embodiments and of being practiced and carried out in various ways which will become obvious to those skilled in the art on reading this disclosure. Also, it is to be understood that the phraseology and terminology employed herein are for the purpose of description and should not be regarded as limiting.

As such, those skilled in the art will appreciate that the conception upon which this disclosure is based may readily be utilized as a basis for designing and carrying out the present disclosed system and eyewear apparatus. It is important, therefore, that the claims be regarded as including such equivalent construction and methodology insofar as they do not depart from the spirit and scope of the present invention.

BRIEF DESCRIPTION OF DRAWING FIGURES

Figures 31, 32, 33:
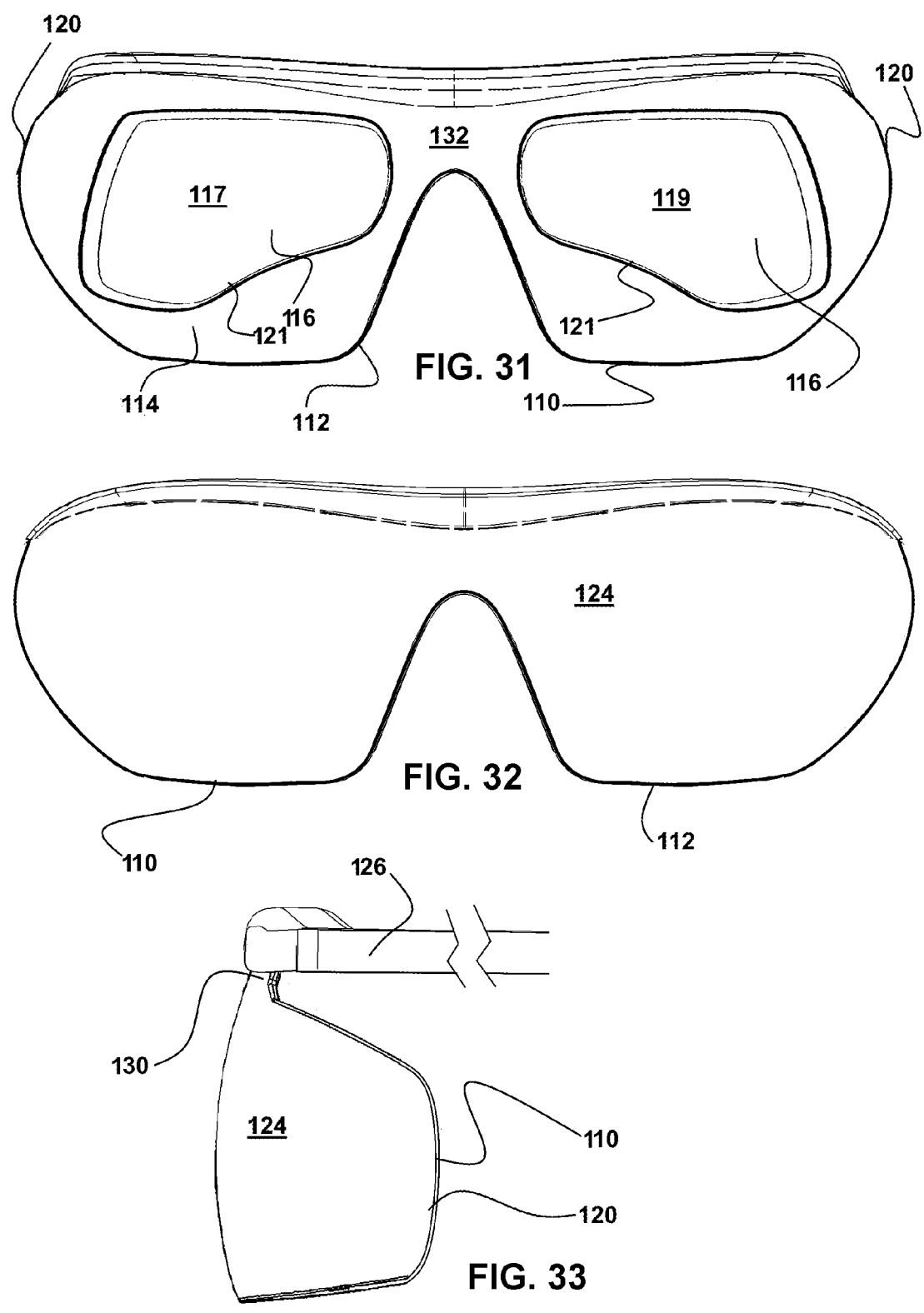
FIG. 31 depicts another mode of the lens device herein showing that the perimeter of the panoramic first lens portion can be formed to accommodate smaller surrounding areas.
FIG. 32 shows a front view of the lens device similar to that in FIG. 28.

FIG. 33 depicts a lens device holder, which may be employed to operatively position any of the lenses herein in front of the eyes of a user in a position spaced from the eyes of the user, which is substantially the same as the lenses herein will be positioned in a chosen AR or VR headset to allow for determination of the proper pupillary distance (PD) and the correct formation of each lens to correct the vision of the eyes of the user.

Other aspects of the present invention shall be more readily understood when considered in conjunction with the above noted accompanying drawings, and the following detailed description, neither of which should be considered limiting.

DETAILED DESCRIPTION OF THE PREFERRED EMBODIMENTS OF THE INVENTION

Figures 1, 2:
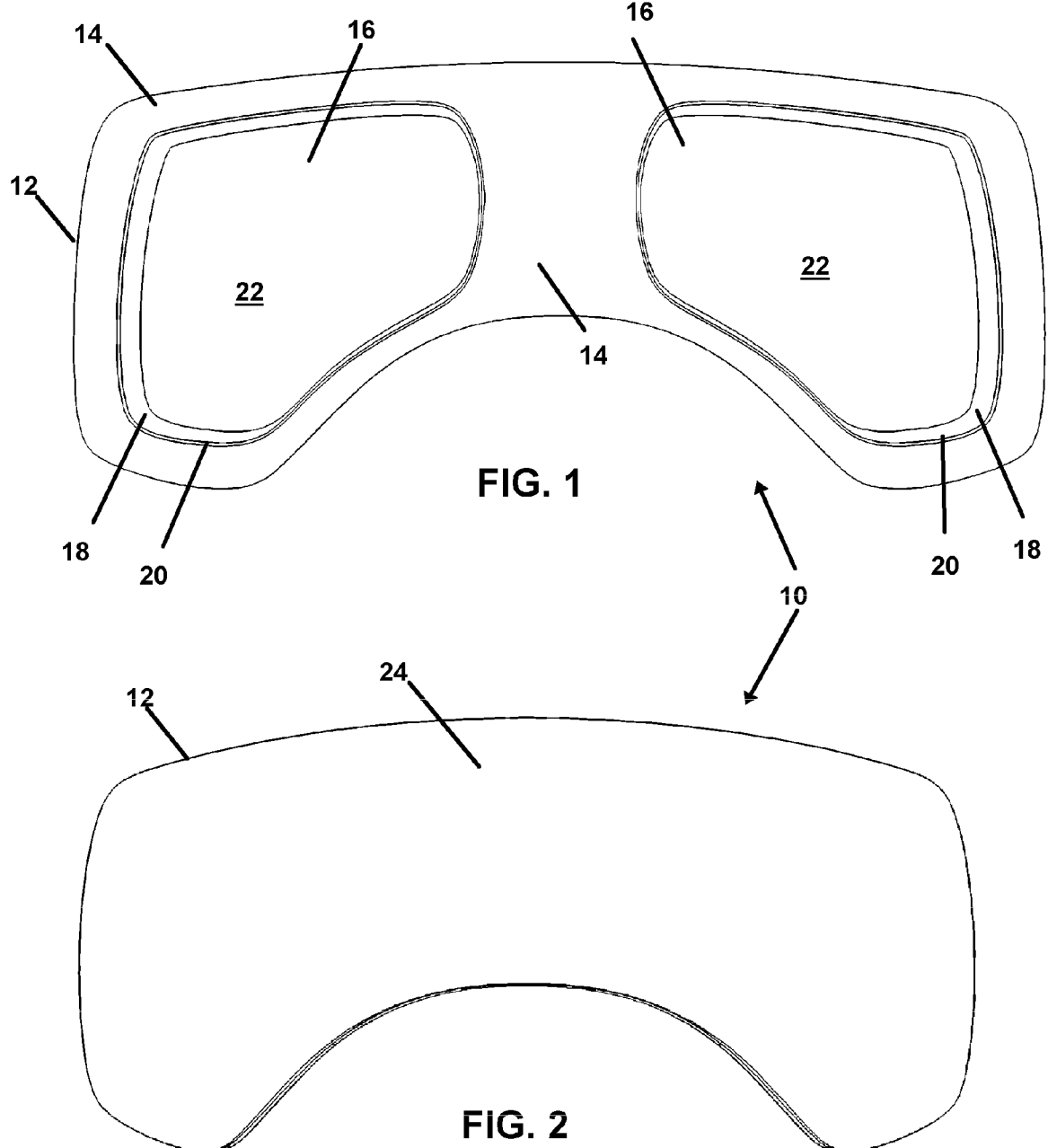
FIG. 1 depicts a view of the first surface of a first lens portion having a plurality of raised portions with shapes defined by a perimeter sidewall, extending away therefrom.
FIG. 2 depicts a view of the opposite side of the first lens portion from FIG. 1 showing the second surface and the shadowless appearance of the second surface provided by the unitary structure herein.

Now referring to drawings of FIGS. 1-33, where similar structures are described with like numerals, there is seen in FIG. 1 a view of a mode of the device 10 having a unitary structured lens formed of a first lens portion 12 having a first surface 14 and having at least one or, as shown preferably, a plurality of projecting or projecting portions 16 extending therefrom. The projecting portions 16 have a shape defined by a perimeter formed by a sidewall 18 which extends away from an intersection 20 at a first end of the sidewall 18 with the first surface 14 of the first lens portion 12. The sidewall 18 of each projecting portion 16 extends to a distal end at an intersection with the edge of a projecting surface 22, formed within the perimeter defined by the sidewall 18. The projecting surface 22 is adapted for formation of an ophthalmic lens to correct the vision of a user or wearer.

A particularly preferred shape of the projecting portions 16 is shown in FIG. 1. As shown, each of the two projecting portions 16 has a respective wider diameter adjacent the opposing two ends of the curved first lens portion 12, and have narrower diameters at their respective ends, adjacent the central portion 32.

This preferred shape allows for portions of the projecting portions 16 to extend closer to the bridge of the nose in this central area 32 while concurrently extending to the temple and well below the nose. This extended rectangular shape, with a curve extending from a nose-side of the projections 16 to a lower edge adjacent both ends of the first lens portion 12, allows for formation of progressive lenses, using the projecting portions 16, and prescriptive eyewear, which are highly customized, as the formed progressive lens can be both horizontal from top to bottom and sideways from nose end to temple end.

FIG. 2 depicts a view of the opposite side or second side surface of the first lens portion 12 from that shown in FIG. 1. A novel aspect of the disclosed device 10 is that the formed unitary structure of ophthalmic lens formed on the projecting portion 16 projecting from the first side 14 of the first lens portion 12, when viewed from the second surface 24 side, yields a shadowless appearance of the second surface 24 even where a filter material may be inserted as noted below.

Figures 3, 4, 4A, 4B, 4C, 4D:
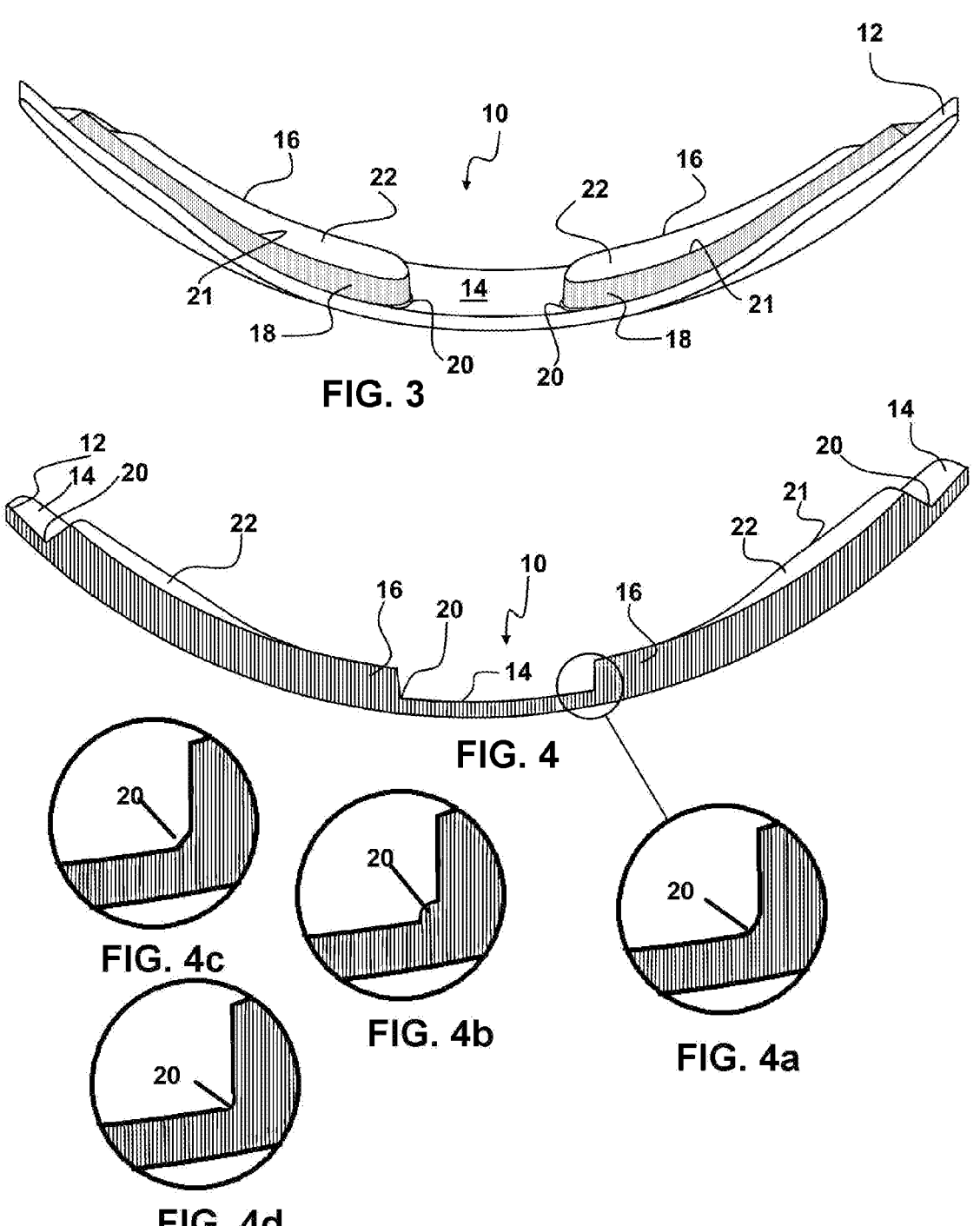
FIG. 3 depicts a perspective view of the view of FIG. 1 showing two projecting portions having a shape defined by a perimeter sidewall extending from the first surface of the first lens portion.
FIG. 4 is a sectional view through FIG. 3 showing the unitary structure formed by the projecting portions and first lens portion and the non linear intersection of the sidewall of the projecting portions with the first surface of the first lens portion.
FIG. 4a shows a curved intersection between the sidewall defining the shape of the projecting portion and the first surface of the first lens portion.
FIG. 4b shows a reverse curved intersection between the sidewall defining the shape of the projecting portion and the first surface of the first lens portion.
FIG. 4c shows an angled intersection between the sidewall defining the shape of the projecting portion and the first surface of the first lens portion.
FIG. 4d shows a curved radius relief intersection between the sidewall defining the shape of the projecting portion and the first surface of the first lens portion.

Shown in FIG. 3 is a perspective view of the device 10 shown in FIG. 1. Depicted are a plurality of two projecting portions 16 each having a shape defined by the perimeter of a sidewall 18 extending from an intersection 20 with the first surface 14 of the first lens portion 12. As can be seen the cross sectional thickness of the first lens portion 12 surrounds the formed projecting portions 16 and is significantly thinner. As noted, the projecting portions 16 and first lens portion 12 are formed in a unitary structure, either by a single mold with the projections 16 and lens portion 12, or by co molding formed projecting portions 16 into the mold for the first lens portion 12 which melts and forms the projecting portions 16 into the structure of the first lens portion 12.

In the depiction of FIG. 4 is shown a sectional view through the device as in FIGS. 1 and 3 showing the unitary structure of the first lens portion 12 and projecting portions 16. The non linear intersection 20 of the sidewall 18 forming the perimeter and defining the shape of the projecting portions 16 with the first surface 14 of the first lens portion 12 is preferred. As noted above, the non linear intersection 20 of the sidewall 18 with the first surface 14 is most important. By non linear is meant that the line running along the surface of the sidewall 18 running between its communication with the raised surface 22 and the intersection 20, does not intersect the line or planar surface of the first side of the first lens portion.

Instead, at or adjacent to, the intersection 20 of the surface of the sidewall 18 deviates from a planar or straight surface, with an angled portion or curved portion of the surface communicating between the sidewall 18, and the first surface 14. Currently, the angled intersection of FIG. 4c and the curved intersection is in FIG. 4a are particularly preferred as a non linear communication of the sidewall 18 with the first surface 14, however the other noted intersection shapes of FIGS. 4b-4d are also examples of a non linear communication of the sidewall 18 at or adjacent to the first surface 14.

FIG. 4a shows a curved surface at the intersection 20 between the sidewall 18 defining the shape of the projecting portion 16 and the first surface 14 of the first lens portion 12.

FIG. 4b shows a reverse curved shape of the surface of the intersection 20 between the sidewall 18 defining the shape of the projecting portion 16 and the first surface 14 of the first lens portion 12.

FIG. 4c shows an angled surface of the intersection 20 between the sidewall 18 defining the shape of the projecting portion 16 and the first surface 14 of the first lens portion 12.

FIG. 4d shows a curved relief shaped intersection 20 of the perimeter edge of the sidewall 18, running underneath the first end of the sidewall, 18 and depending into the first surface 14, and running for the perimeter of the projecting portion 1.

Thus, the non linear intersection, as defined herein, can be any of a group of non linear intersections including an intersection formed by a curved surface extending between said first end of said sidewall and said first surface of said first lens portion, as in FIGS. 4a and 4b, and an intersection formed by an angled surface extending between said first end of said sidewall and said first surface of said first lens portion, as in FIG. 4c, and an intersection formed by a recess extending underneath said first end of said first sidewall 18 and depending into the first surface 14 of said first lens portion 12. This formation of a non linear intersection as noted, prevents cracks.

Figures 5, 6:
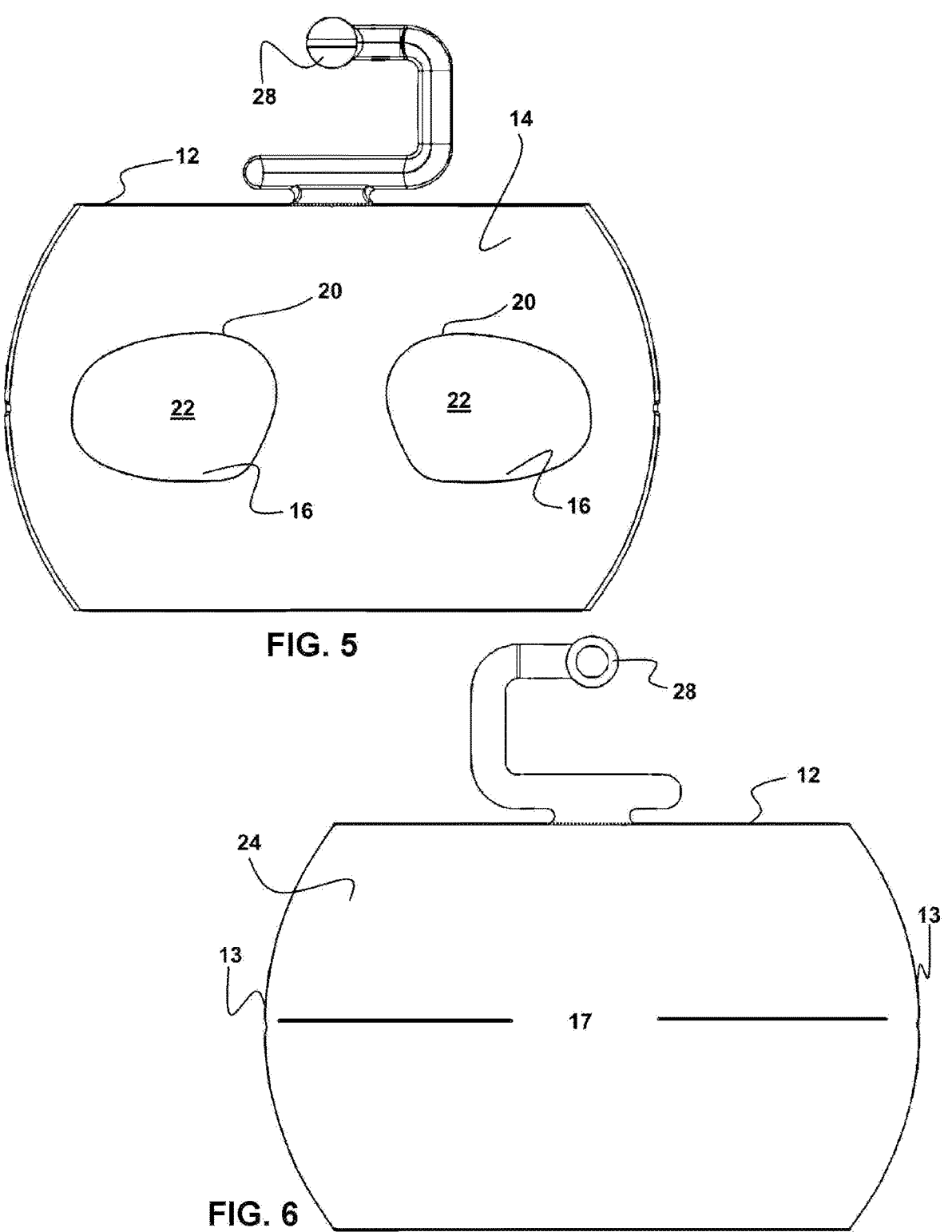
FIG. 5 depicts another mode of the unitary lens structure showing a curved panoramic first lens portion and two circular projecting portions extending from the first surface thereof and showing the centered positioning of a tooling engagement member attached thereto, which may be employed on all versions of the device herein.
FIG. 6 shows a view of the unitary lens structure of FIG. 5 from the opposite side from FIG. 5 showing the second side surface.

As shown in FIG. 5 is depicted another mode of the unitary lens structure device 10 herein. Shown is a curved panoramic first lens portion 12 and two circular projecting portions 16 extending from the first surface 14 of the curved first portion 12 of the formed lens. The perimeter intersection 20 of both sidewalls 18 is shown also and would preferably non linear as noted above. Additionally depicted is a centered tooling engagement member 28 in operative engagement to the first lens portion 12 along a side edge. This tool engagement member may be employed in all modes of the device herein.

In FIG. 6 is shown an opposite side view of the unitary lens structure of FIG. 5 showing the second side surface 24 and showing the tooling engagement member 28 centered between the two side edges 13 of the first lens portion 12 and extending perpendicular to a horizontal axis running between the two side edges 13.

Figure 7:
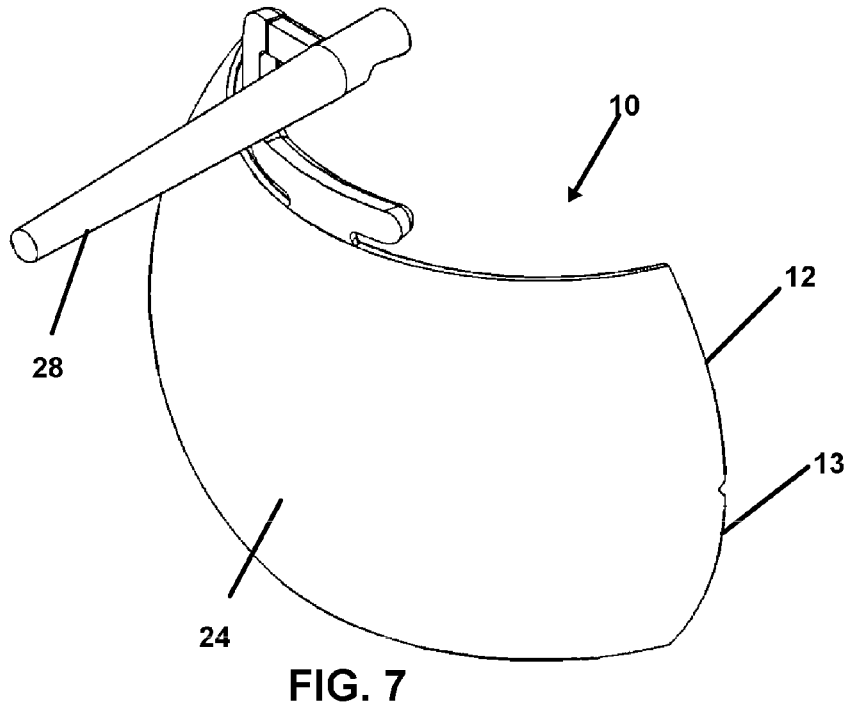
FIG. 7 shows a perspective view of a unitary lens structure such as in FIG. 6, showing the tooling engagement member centered between the two ends of the first lens portion and running perpendicular to an axis running across the first lens portion.

A perspective view of this configuration is shown in FIG. 7. As can be seen, the tooling engagement member 28 is centered between the two ends 13 of the first lens portion 12 and runs substantially perpendicular to an axis 17 running across the first lens portion 12 between both ends or the temple ends thereof. As noted, this tooling engagement member 28 is adapted for engagement with conventional eyeglass grinding machines, where a goggle lens will not fit or be engageable to form the lenses.

Figures 8, 9, 10:
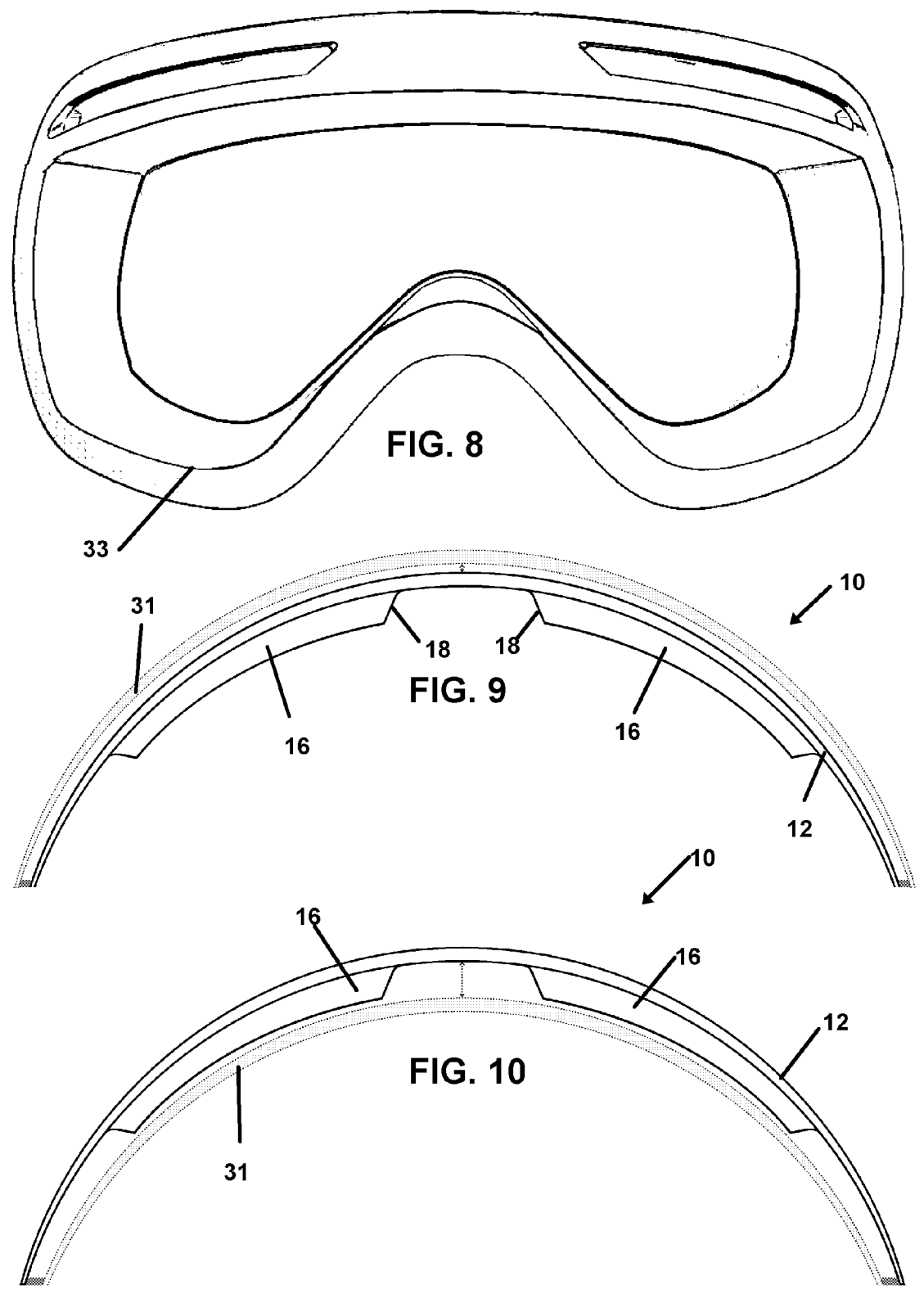
FIG. 8 depicts a sport goggle mode of the device herein.
FIG. 9 depicts a first lens portion having two projecting portions thereon and a second lens engaged in a spaced relationship adjacent the second surface of the first lens portion as would be engaged in the goggle of FIG. 8.
FIG. 10 shows the device in a similar fashion to that of FIG. 9, engageable within the goggle frame of FIG. 8, wherein the second lens forming a cavity is positioned adjacent to the raised lens-machinable surfaces of the projecting portions.

FIG. 8 depicts a sport or protective goggle mode 33 of the device 10 herein. The configurations shown in FIGS. 9-12 can be engaged with a goggle frame such as in FIG. 8.

In FIG. 9 is shown a first lens portion 12 having two projecting portions 16 thereon and having a second lens 31 engaged in a spaced relationship adjacent the second surface 24 of the first lens portion 12 as would be engaged in the goggle of FIG. 8.

Shown in FIG. 10 is a mode of the device 10 similar in fashion to that of FIG. 9 and engageable within the goggle frame 33, such as that of FIG. 8. In this figure, the second lens 31 forming a cavity is positioned adjacent to the lens-machinable raised surfaces 22 of the projecting portions 16.

Figure 11:
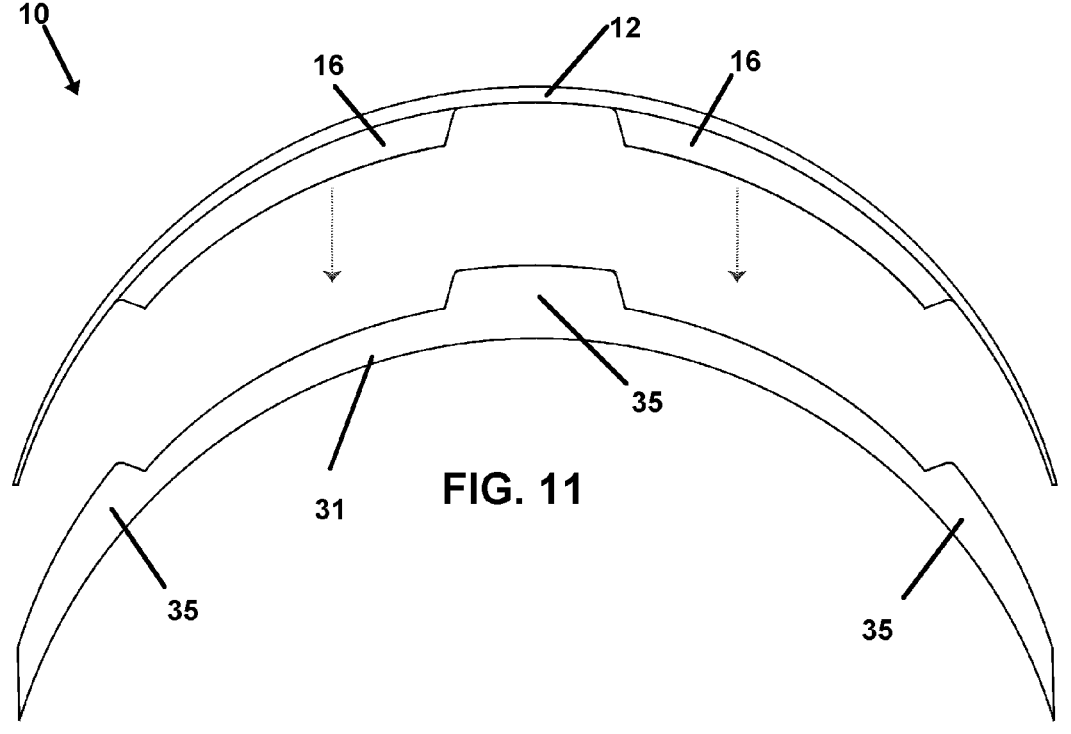
FIG. 11 shows another mode of the device adapted for a goggle to minimize fogging in the same fashion as those of FIGS. 9, 10, and 12, and showing a mating lens having projecting sections adapted to fit adjacent the sidewalls of the formed projecting portions of the first lens.
Figures 12, 13, 14, 15A, 15B, 15C, 15D:
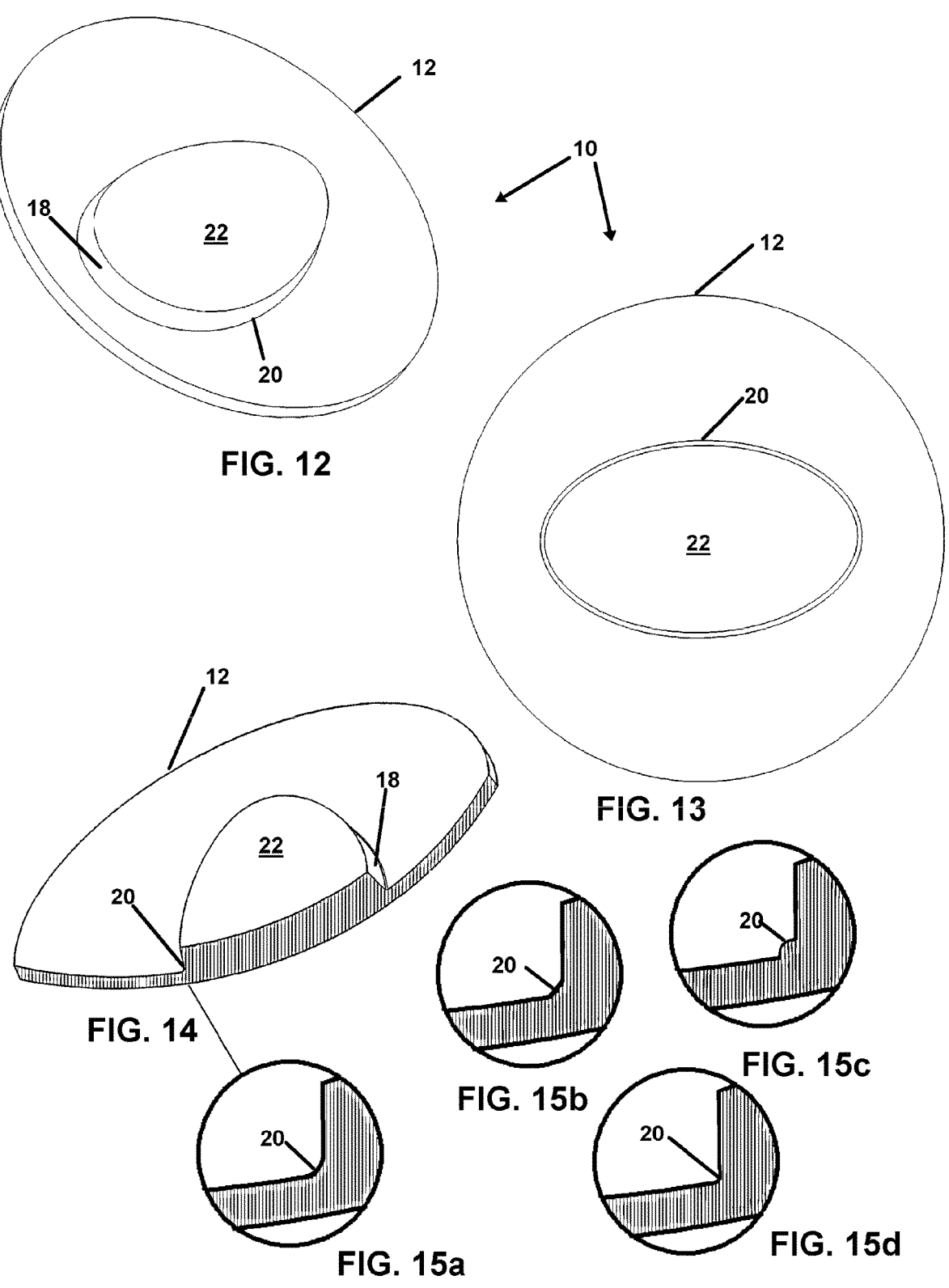
FIG. 12 depicts a mode of the device forming a unitary lens structure which is adapted for engagement in eyeglass frames where the thinner cross section of the first lens portion surrounds the thicker area where the projecting portion is engaged.
FIG. 13 is an overhead view of the device as in FIG. 12 showing the intersection surrounding the perimeter sidewall defining the shape of the oval projecting portion and the first surface of the first lens portion.
FIG. 14 depicts a sectional view of the device of FIGS. 12 and 13 and shows the preferred non linear intersection of the sidewall defining the projecting portion, with the first surface of the first lens portion.
FIGS. 15a-15d depict various preferred shapes to the intersection of the sidewall with the first surface of the first lens portion to eliminate the linear intersection prone to cracking.

Another goggle or protective eyewear mode is shown in FIG. 11 and adapted to minimize fogging in the same fashion as those of FIGS. 9, 10, and 12. As depicted, a mating second lens 31 having projecting sections 35 is engageable where the projecting sections 35 are configured to fit adjacent the sidewalls 18 of the formed projecting portions 16 of the first lens 12 and fill the gaps.

FIG. 11 shows another mode of the device adapted for a goggle to minimize fogging in the same fashion as those of FIGS. 9, 10, and 12, and showing a mating lens having projecting sections adapted to fit adjacent the sidewalls of the formed projecting portions of the first lens.

FIG. 12 depicts a mode of the device forming a unitary lens structure formed with a first lens portion 12 and projecting portion 16 as with the other modes herein. This mode of the device is well adapted for engagement in eyeglass frames where the thinner cross section of the first lens portion 12 which surrounds the thicker area where the projecting portion 16 rises will better fit frames.

FIG. 13 is an overhead view of the device as in FIG. 12 showing the perimeter intersection 20 of the sidewall 18 with the first surface 14 of the first lens portion 12. As depicted, the sidewall 18 defines an oval projecting portion 16 extending from the first surface 14 of the first lens portion 12.

FIG. 14 depicts a sectional view of the device of FIGS. 12 and 13 and shows the preferred non linear intersection 20 between the sidewall 18 and the first surface 14 of first lens portion 12 as is preferable in all modes of the device herein.

FIGS. 15a-15d depict various non linear shapes to the intersection 20 of the sidewall 18 with the first surface 14 of the first lens portion 12. Such, as noted, are highly preferred to eliminate a linear intersection prone to cracking.

Figures 16, 17:
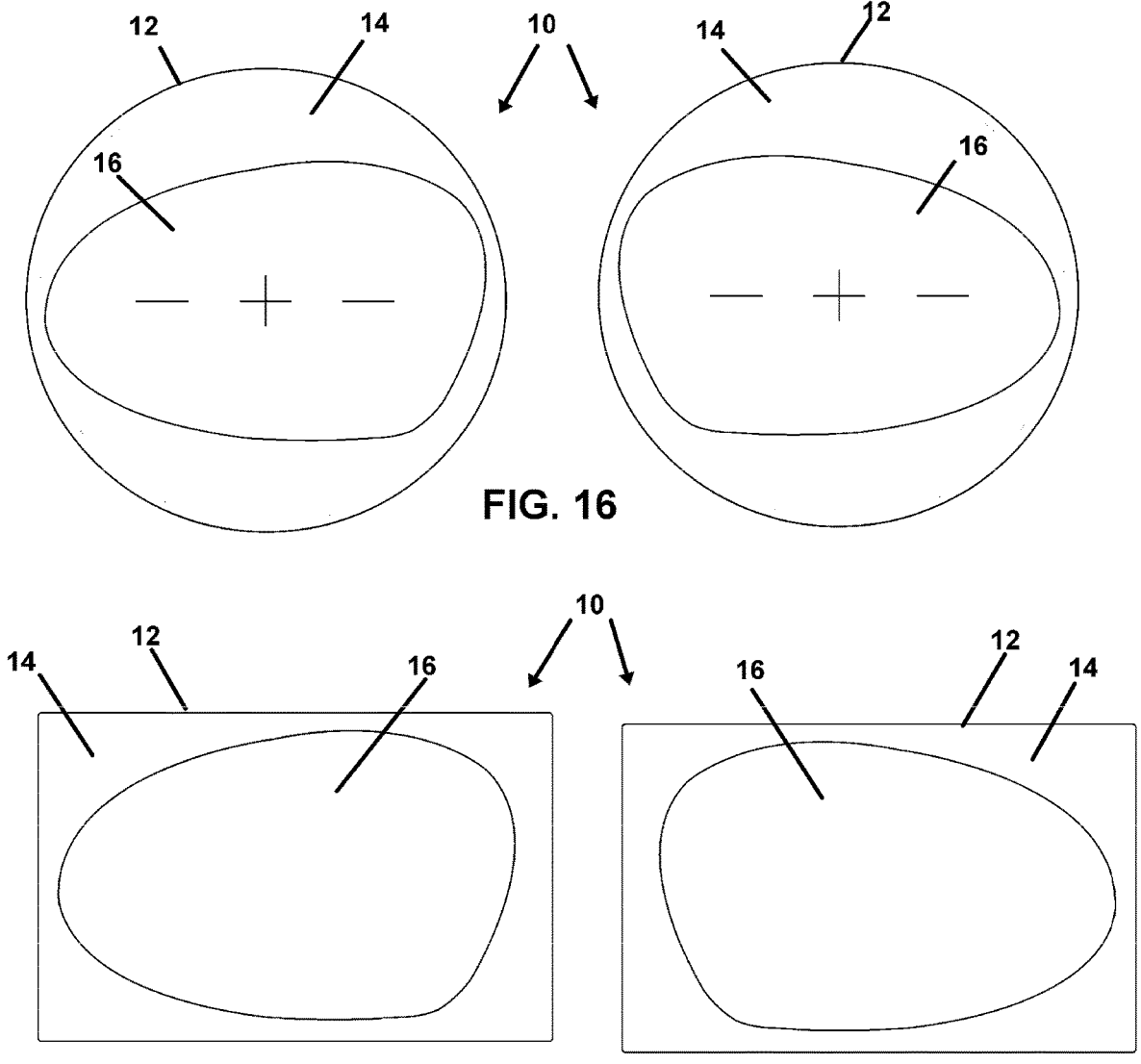
FIG. 16 depicts unitary lenses formed to engage eyeglass frames where the thicker projecting portion is surrounded by the thinner first lens surface to allow engagement to more fashionable eyewear when the user must have thick lenses for sight correction.
FIG. 17 depicts another mode of the device as in FIG. 16 but with rectangular panoramic first lens portions.
Figure 18:
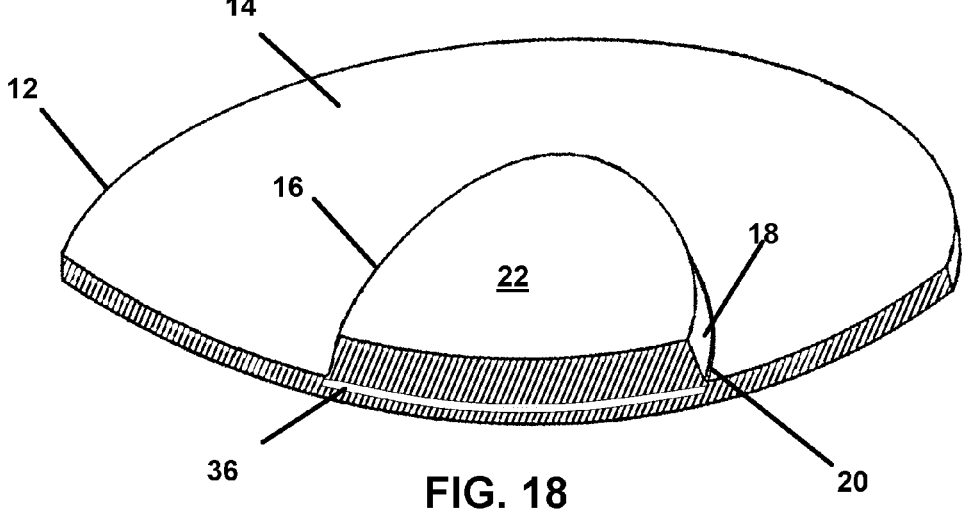
FIG. 18 shows the unitary lens structure herein having a polarizing or other filter engaged between the projecting portion and the first lens portion and which can be included with any form of the unitary lens herein.
Figure 19:
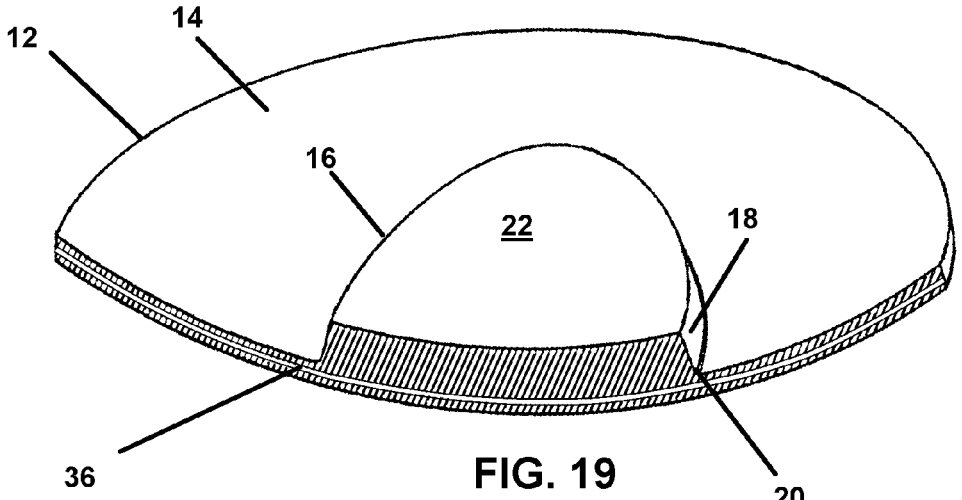
FIG. 19 depicts the unitary lens structure where the polarizing or other filter layer is positioned across the entire first lens component in between the first surface and second surface thereof.

FIG. 16 depicts unitary lens devices 10 formed to engage eyeglass frames where the thicker projecting portion 16 is surrounded by the thinner first lens portion 12 to allow for optical prescriptions requiring thick lenses but also allow engagement of the formed lens devices 10 to more fashionable eyewear when the user must have such thick lenses for sight correction. In FIG. 17 is shown a similar mode of the device 10, as in FIG. 16, but with rectangular panoramic first lens portions 12.

Where filtered optics are desired or required in the device 10 herein in any mode, such is depicted in FIG. 18 and FIG. 19. In FIG. 18 is shown the unitary lens device 10 which has a polarizing or other filter layer 36 engaged between the projecting portion 16 and the second side 24 of the first lens portion 12. Shown in FIG. 19, the polarizing or other filter layer 36 is positioned across the entire first lens portion 12 in between the first surface 14 and second surface 24 thereof.

Figure 20:
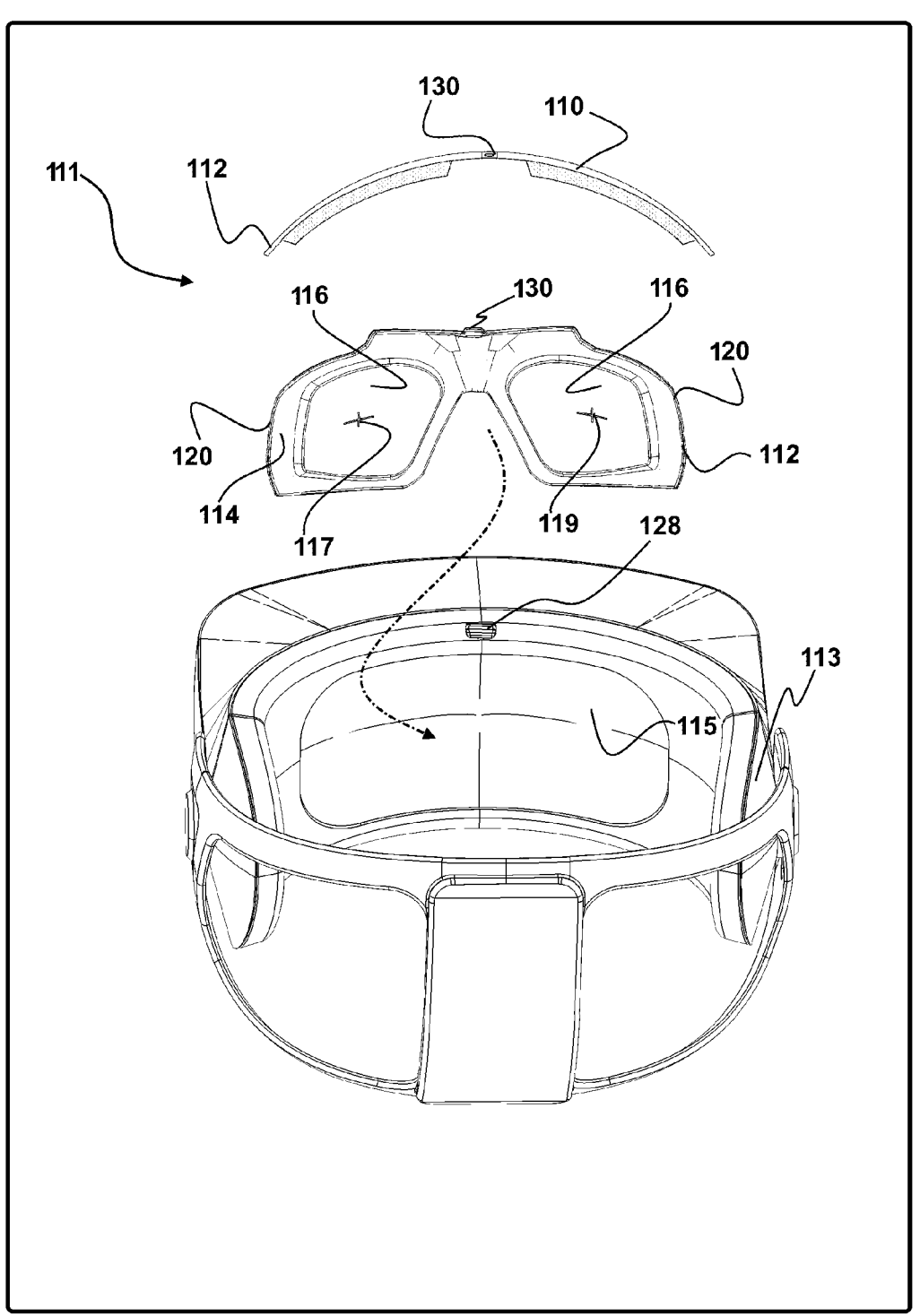
FIG. 20 depicts an exploded view showing the headset lens system having a lens device ready for insertion to a mount with an AR or VR headset having a curved display to provide the user vertical and panoramic corrected vision.

There is seen in FIG. 20 an exploded view of the lens system 111 herein showing the lens device 110 herein ready for insertion to an operative mount or engagement with an AR or VR eyewear or headset having a curved display 115 or other AR or VR eyewear. The lens device 110, as can be discerned, has the same optical properties and vision correction properties and functions as that of the lens of FIG. 1-2 or 8-11, in that the projection or projections 116 extending from the first surface 114 of the first lens portion 112 curve with the first lens portion around the face and eyes of a user. They are thus formable in the same fashion as those of FIG. 1-2 or 8-11 to ophthalmic lenses having vertical progressive correction and horizontal vision correction around the curve of the face of the user to both sides.

The lens device 110 is configured for engagement and use in the same manner as that of FIGS. 1-10 but may also include means for operative engagement to an AR eyewear or headset or VR eyewear or headset. This operative engagement positioning will allow the user to view the AR or VR video and/or augmented reality displayed through the corrective lenses formed using the first lens portion 117 and second lens portion 119, which are formed from the projections 116 which both wrap around their eyes and face. By AR eyewear or headset or VR eyewear or headset herein is meant any face-worn headset which provides the user a video display therein for electronic depiction of video, such as, for example, the Apple Vision Pro, or the Meta Quest, or the Sony VR2 or other such headsets. By AR or VR eyewear or headset is also meant herein any augmented reality or virtual reality eyewear configured for positioning on the head of a user, which is not a goggle style, such as those manufactured by castAR of Palo Alto, California and similar eyeglass style AR or VR eyewear.

The curved lens device 110, in a similar fashion to those of FIGS. 1-2 and 8-10 and other figures shown herein, has one or a plurality of projections or projecting portions 116 thereon extending from the first surface 114 of the first lens portion 112. In the same manner, these projections 116 curve around the eyes of the user when the lens device 110 is mounted to an as-used position in front of the eyes of the user. There are wider portions of each projection 116 adjacent each side edge 120 of the first lens portion 112 to provide periphery vision correction for the user and narrower portions toward the central area 132 of the first lens portion 112 to allow for positioning of the nose of the user. So operatively engaged with eyewear or AR or VR eyewear, the lens device 110 provides the user both vertical and horizontal or panoramic corrected vision as graphically depicted in FIGS. 26-30.

As such, when wearing the AR or VR headset 113, with the lens device 110 operatively mounted to an as-used position therewith, the user may turn their eyes to focus on different areas of the display 115 and have their vision corrected by the curving ophthalmic lenses formed from one or two projections 116 located on the first surface 112 of the curved or panoramic first lens portion 112. It should be noted that the lens device 110 may also be mounted to a goggle or frame or the like in a similar fashion to that of FIGS. 1-2 and 8-11 but may also have connectors 130 and mounts 128 or other means for engagement to the AR or VR headset 113 thereby allowing use for both.

Figure 22:
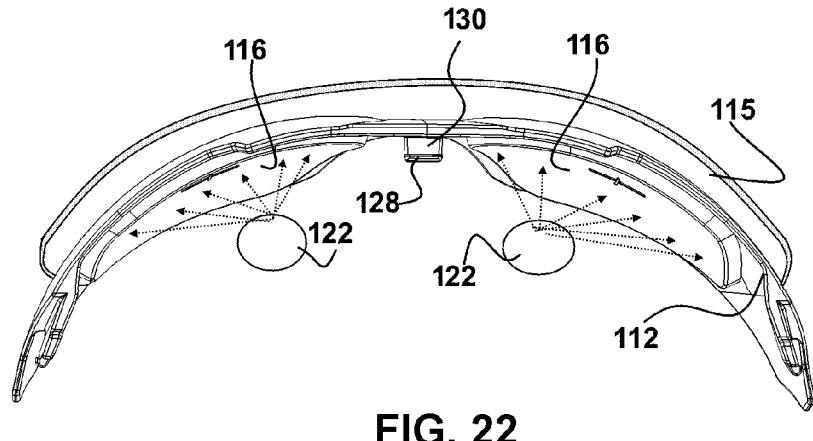
FIG. 22 depicts the vision correction provided to the eyes of the user by the device herein with both panoramic correction to the sides and vertical correction, whereby the user can see the periphery of the AR or VR display clearly.

As can be seen in other drawings herein, such as in FIG. 22, the first lens portion 112 is formed of optically correct material in a curving or panoramic shape such that the two opposite edges 120 extend adjacent to or past the temple area on the opposing sides of the head of the user with the lens device 110 in an as-used position. The projection 116 or the projections 116, formed as a unitary structure and part of the first lens portion 112, curve around from a central area 132 adapted for positioning of the nose of the user therein to an edge of the projections at or adjacent the side edges 120 of the curved or panoramic first lens portion 112.

It is the unitary structure of the optically correct panoramic first lens portion 112 and the curved projection 116 or projections 116 extending from the rear surface thereof facing the eyes of the user, when worn, which is especially preferred to help eliminate refractive errors, double images, rainbows, and other vision issues which are caused by wearing eyeglasses behind a front lens as well as to eliminate uncorrected peripheral vision.

Once the projection or projections 116 are formed to an ophthalmic lens to correct the vision of the wearer or user, they will have vertically corrected vision up and down such as progressive, and they will have panoramic horizontal corrected vision side to side. Thus, the user, wearing the lens device 110 herein, an the as-used position operatively engaged with or to a AR or VR type headset 113, will be afforded corrected vision of the display 115 forward and toward both side edges 120, by simply turning their eyes in that direction.

As noted, conventionally, a user wearing conventional eyeglasses will have an effective corrected vision field of view to substantially between 90 and 115 degrees. This leaves blurry and uncorrected vision at their periphery viewing and they must turn their head to see clearly to the sides. Such will not work when wearing an AR or VR headset. Such is neither desirable or recommended when participating in sports, such as bicycle racing or skiing, where the user would need to turn their head to see to the sides, which takes their attention off the area directly in front of them where they are headed at high speed.

As can be seen in FIGS. 26-27 and 29-30 as well as in FIGS. 1-2 and 8-11, the curving projection or projections 116 herein are thus formable to provide ophthalmic lenses for vision correction in the horizontal field of view of the user to a range of at least 130 and up to 180 degrees depending on how far the user can rotate their eyes side to side. Further, their vertical vision correction is also provided along this horizontal range by forming the projections 116 wider adjacent to two side edges 120.

Figure 21:
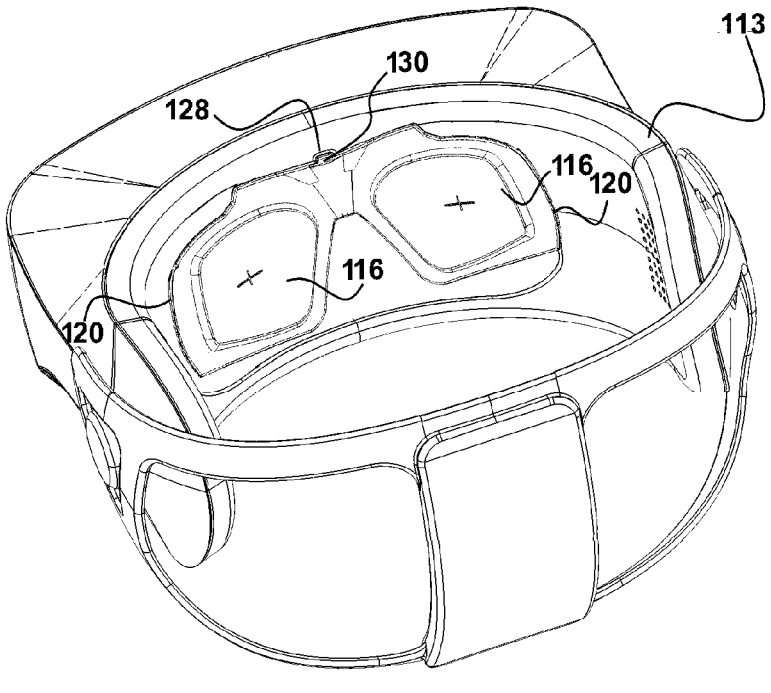
FIG. 21 shows the lens device of FIG. 20 engaged to the AR or VR headset to provide corrected vision to the user therethrough.

FIGS. 21-22 show the lens device 110 of FIG. 20 engaged to the AR or VR headset 113 to provide the concurrent horizontal or panoramic and vertical corrected vision to the user therethrough. Thus, as shown in FIG. 22, with the headset 113 positioned in an as-used position which locates the eyes 122 of the user adjacent the display 115, and the lens device 110, the user is afforded corrected vision vertically and horizontally around the cure of the panoramic first lens portion 112. Thus, unlike eyeglasses, the device 110 provides corrected vision to the user on the periphery or sides of their head as well as forward and vertically top to bottom, by simply moving their eyes, and not their head.

As also shown in the modes of the lens device 110 of FIGS. 20-24, it may be removably engageable to an operative position adjacent one or two displays 115 of the headset 113. This mode of the lens device 110 works well to allow each individual user to have their own lens device 110 where the one or two projections 116 extending from the rear surface of the panoramic first lens portion 112 are formed to yield the ophthalmic lens for vision correction they need to see the display 115 clearly. By formed is meant ground or cut or 3D printed or otherwise changing the shape of the surface of the projection 116 or projections to form a lens having the curvature to correct the vision of the user such that they see clearly through the formed cured projection extending from the unitary structure with first lens portion 112.

Such a removably engageable configuration will allow eye professionals, having a mount 126 such as in FIG. 33, to prescribe, form, and check the formed ophthalmic lens for vision correction of each lens device 110 remotely for each user. The frame mount 126 would position the lens device 110 in substantially the same position in front of the eyes of the user as it would eventually be positioned within the headset 113 of choice, such as in FIGS. 21-23 or in conventional eyeglass frames having a center frame and temples for engagement on the sides of the head of a user.

In this fashion, once the projections 116 are formed by conventional grinding, abrasive surfacing, or 3D printing or other means to form ophthalmic corrective lenses for the impaired vision of each user, they may be tested locally for correctness as to vision correction vertically and panoramically. A mount 128 on the headset 113 will be positioned to operatively engage with a connector 130 on the lens device 110, such that it removably engages with the headset 113 and places the lens device 110 in an as-used position. The connector 130 may be a removable connection between the first lens portion 112 and the headset 113 or a goggle or frame also which will hold the device 110 in the as used position and allow for adjustment of the first lens portion 112 toward and away from the face and eyes of the user. Such will allow for translation of the first lens portion 112 and the processed projections 116 to locate them in the best distance from the eyes of the user to focus through the ophthalmic lenses formed by the processing of the projection or projections 116.

Figures 25, 26, 27:
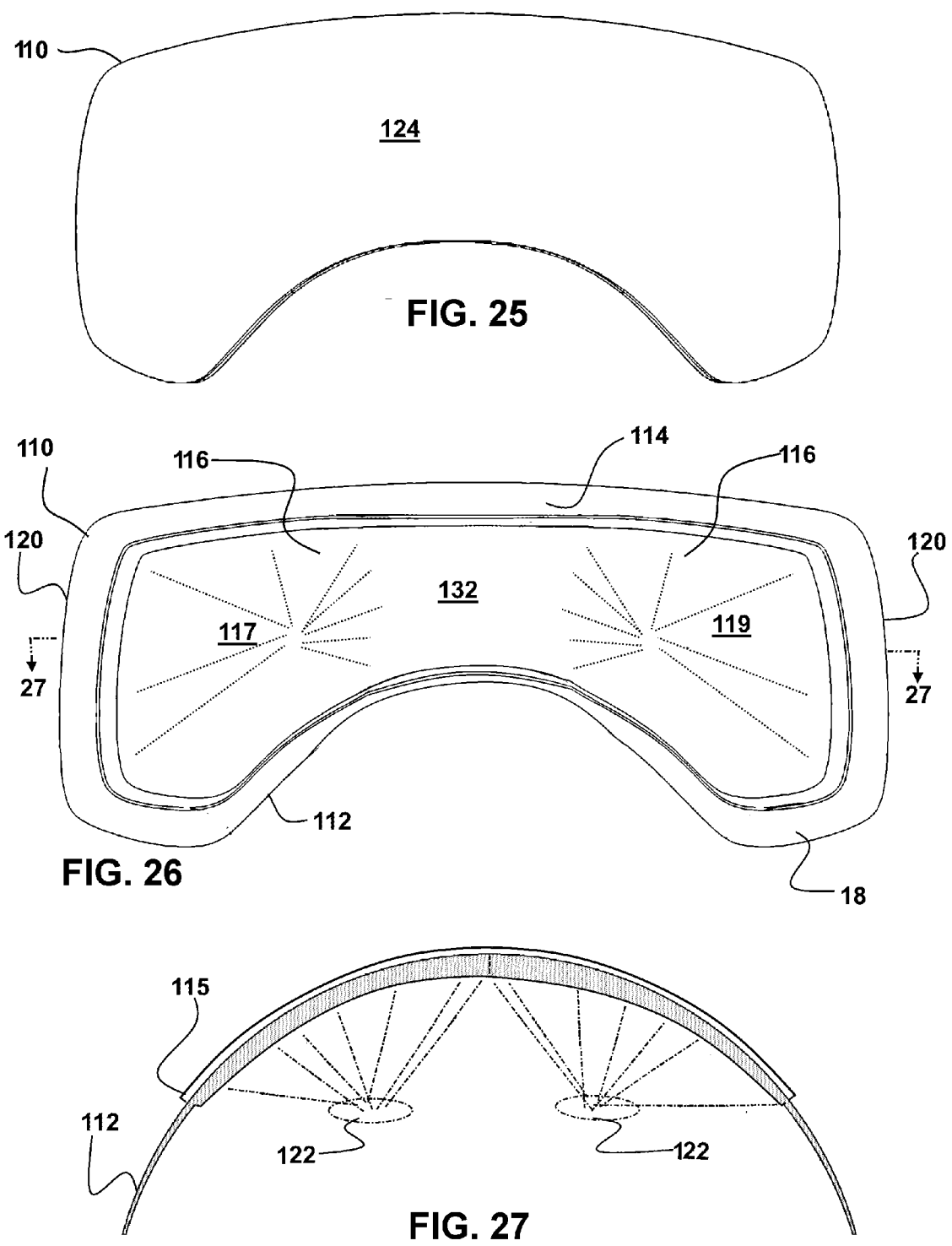
FIG. 25 depicts a mode of the device herein formed in a combination with or removably engageable with a panoramic display screen yielding panoramic and vertical vision correction.
FIG. 26 depicts a projection extending from the side of the panoramic lens of the device herein wherein two corrective lens areas are formable to provide vision correction to both eyes of the user.
FIG. 27 depicts a sectional view of the device of FIGS. 25-26 showing the panoramic vision correction for both eyes of the user provided when the projection is formed for such.
Figures 28, 29, 30:
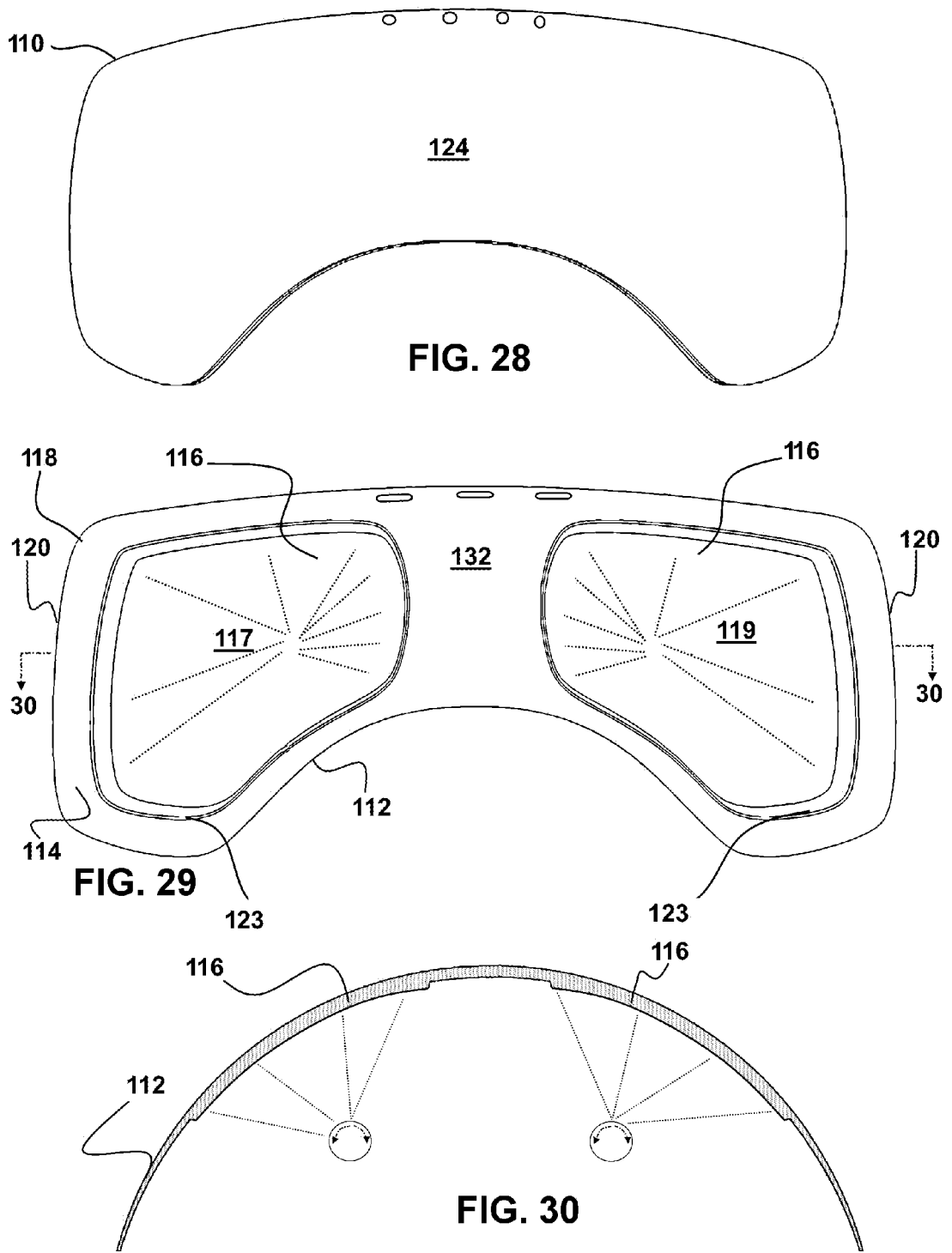
FIG. 28 depicts a view of a mode of the lens device herein from the side of the panoramic first lens on which the one or two correcting projections are extended from the opposite side, such as in FIG. 29.
FIG. 29 shows a first corrective lens portion positioned adjacent the second corrective lens portion and showing the larger respective sections thereof adjacent the right and left edges of the first lens to provide vertical and panoramic vision correction to both eyes.
FIG. 30 is a sectional view through the lens device herein, such as in FIG. 20 or FIG. 29, showing the first corrective lens portion and second corrective lens portion formed in the unitary structure with the panoramic first lens and providing the user vertical progressive and eye-turning panoramic correction of vision, as in FIG. 22.

By as-used position herein is meant that the lens device 110 is aligned with and adjacent the display 115 area when employed in combination with an AR or VR device, and, for all modes of the device 10 or 110, it is optically aligned to thereby position one respective formed raised portion 116 in front of the aligned eyes 122 of the user, such as in FIG. 2, 27 or 30.

For fine tuning of the lens device 110 to the eyes of the user and the headset 113 to which it is engaged, or to the eyeglass frame or goggle, an adjustable mount 131 may be provided. The adjustable mount 131 may have an adjuster which can be actuated to move the lens device 110 closer to or further from the display 115 and concurrently closer or further from the aligned eyes of the user.

Figures 23, 24:
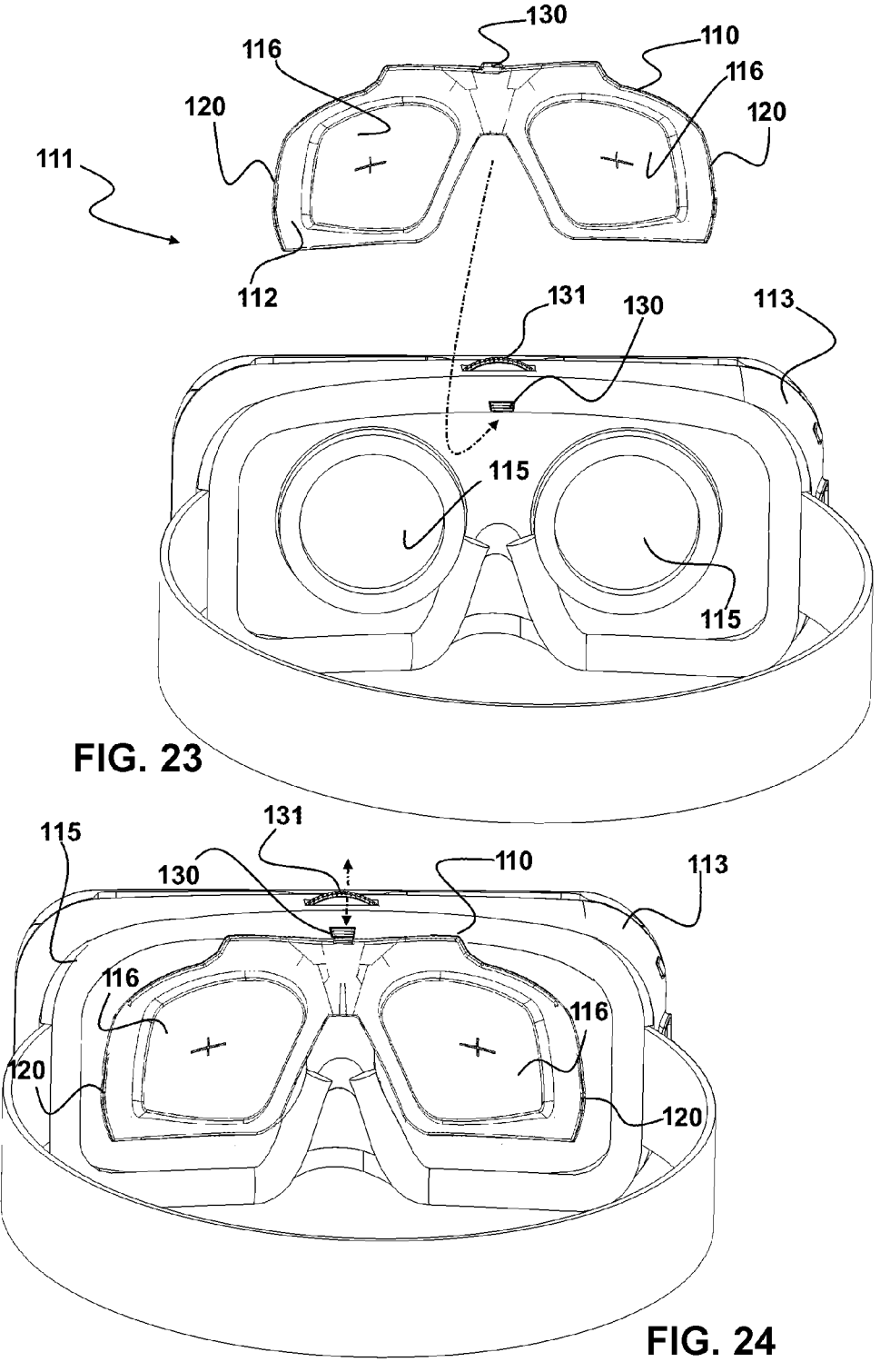
FIG. 23 shows the lens device herein ready for operative engagement with a dual display type AR or VR headset.
FIG. 24 shows the device, as in FIG. 23, operatively engaged with the headset, such as the type in FIG. 20 or 23.

Shown in FIG. 23 is the lens device 110 herein ready for operative engagement with a conventional dual display type AR or VR headset. By operative engagement is meant that the lens is engaged with an eyeglass frame, a goggle, an AR or VR device, or other forms of mounting on the face of a user. This engagement can be by positioning the device in a slot with any frame or in a connection to a mount or connector or slot or other means to hold the lens to an eyewear frame or goggle in a position to align one or both projections 116 with the eyes of the user.

As shown, in one mode, a connector 130 is engageable with either a fixed mount 128, such as in FIG. 22, or an adjustable mount 131, as in FIGS. 23-24. The adjustable mount 131, as noted, allows for translation of the eyewear device 110 closer to and further from the display 115. The adjustable mount 131 may also move the first lens portion 112 of the eyewear device 110 vertically to align it and the ophthalmic lenses formed, as noted herein, in operative alignment with the eyes of the user. The engaged lens device 110 of FIG. 22 is shown in FIG. 24.

The adjustable mount 131 would include a frictional or mechanical engagement of the mount 130 to the first lens portion 112 and gearing or the like which will move the mount 130 engaged to the first lens portion 112 toward and away from the eyes of the user. The same mount 130 can also be connected to gearing or sliding engagement to move the first lens portion 112 up and down should such be required to help center the pupils of the user to the proper central positioning relative to the respective projecting portions 116 which would be formed to ophthalmic lenses to correct the vision of each eye of the user.

In FIGS. 25-27 is depicted a mode of the lens device 110 herein wherein a first lens portion 117 and second lens portion 119 are formed into a single projection 116 extending from the rear surface of the panoramic curved first lens portion 112 in the unitary structure therewith. This mode of the device 110 allows for formation of the projection to yield two different vision correction areas such that the right eye and left eye of the user may have vision corrected in a wider panoramic manner. This allows a central area 132 where the formed right and left corrective lens may meet.

Also shown are the display 115 contacting against or being positioned immediately adjacent the front exterior surface of the first lens portion 112. With the single projection 116 providing a first area 117 and second area 119 to surface or machine and form first and second corrective lens areas, the user is again afforded horizontal vision correction for each eye which extends from the opposing sides of the projection 116 which are adjacent a respective edge 120 of the first lens portion 112 to a central area 132.

Shown in FIGS. 28-30 are views of another mode of the lens device 110 herein. As shown, the projections 116 are wider adjacent the edges 120 of the first lens portion 112. An angled bottom edge 121 of each projection 116 extends upward toward a central area of the first lens portion 112 from lower lens sections 123. This configuration, as noted, is preferred to provide a wider up and down vertical vision correction for the user at the wider ends adjacent the edges of the first lens portion 112 than is possible without the shape.

Shown in FIGS. 32-33 is another mode of the lens device 110 herein showing that the perimeter of the panoramic first lens portion 112 can be formed to accommodate smaller surrounding areas.

In FIG. 33 is depicted an example of the lens device 110 in all modes herein which is engageable with a frame mount 126. The frame mount 126 is configured for a removable engagement to the device 110 similar to that of the mount 128 on the headsets 113 to the connector 130 on the formed lens device 110. This positions the lens device 110 with the second side surface 124 facing away from the eyes of the user.

The frame mount 126, when positioned on a user, is employable to hold the projection 116 or projections 116 in front of the eyes of the user, at substantially the same distance from their eyes as it will be when operatively engaged with an AR or VR headset or positioned in a goggle frame or engaged with a mount having temples. In this fashion, the spacing of the pupillary distance (PD) of the user can be determined by viewing the pupils therethrough and the distance of the lens in front of their eyes can be determined.

Once the needed forming of the projections 116 to yield the ophthalmic lens for the vision correction required by the user to clearly see through them, such as viewing the display 115, is accomplished with the correct PD, the frame mount 126 can be employed to hold the finished lens device 110 operatively in the as-used position upon the face of the user to test it prior to being engaged to a headset 113 or to an eyeglass frame or goggle frame. This testing may be accomplished by positioning a display 115 adjacent the lens while engaged to the frame mount 126 in a fashion substantially similar to the positioning of the lens device 110 in the display 115 of choice of the user.

As noted, any of the different configurations and components shown and described herein can be employed with any other configuration or component shown and described as part of the corrective lens device worn on a head of a user such as a goggle, eyewear, or for use with an AR or VR headset. Additionally, while the disclosed lens invention has been described herein with reference to particular embodiments thereof and components thereof operatively engaged for operation, a latitude of equivalent modifications, various changes and substitutions are intended in the foregoing disclosures and it will be appreciated that in some instance some features, or configurations, or operations of the invention could be employed without a corresponding use of other features without departing from the scope of the invention as set forth in the following claims. All such changes, alternations and modifications as would occur to those skilled in the art subsequent to reviewing this specification, are considered to be within the scope of this invention as broadly defined in the appended claims.

Further, the purpose of any abstract of this specification is to enable the U.S. Patent and Trademark Office, the public generally, and especially the scientists, engineers, and practitioners in the art who are not familiar with patent or legal terms or phraseology, to determine quickly from a cursory inspection the nature and essence of the technical disclosure of the application. Any such abstract included herein is neither intended to define the invention of the application, which is measured by the claims, nor is it intended to be limiting, as to the scope of the invention in any way.

What is claimed is:

1. A corrective lens comprising:

a first lens portion extending in a curve from a first end thereof to a second end thereof;

a central area of said first lens portion in between said first end and second end of said first lens portion;

said first lens portion having a first surface opposite a second surface on an opposite side from said first surface;

a first projecting portion extending from said first surface of said first lens portion, said first projecting portion having a first sidewall thereof extending to a first side surface thereof;

said first projecting portion extending in a first curve from a first side of said first sidewall thereof within said central area of said first lens portion to a second side of said first sidewall thereof located adjacent said first end of said first lens portion;

said first side surface of said first projecting portion being processable to form said first projecting portion to said first corrective lens along said first curve providing horizontal vision correction therethrough along said first curve;

said first side of said first projecting portion processable for vertical vision correction therethrough, between a top of said first sidewall of said first projecting portion and an opposite bottom of said first sidewall of said first projecting portion;

said first side surface of said first projecting portion being processable to form a first corrective lens thereon;

a second projecting portion extending from said first surface of said first lens portion, said second projecting portion having a second sidewall extending to a second side surface thereof;

said second projecting portion extending in a second curve from a first side of said second sidewall thereof within said central area of said first lens portion, to a second side of said second sidewall located adjacent said second end of said first lens portion;

said second side surface of said second projecting portion being processable for curved horizontal vision correction therethrough along said second curve;

said second side surface of said second projecting portion processable for vertical vision correction therethrough, between a top of said second sidewall of said second projecting portion and an opposite bottom of said second sidewall of said first projecting portion; and wherein said first lens portion is operatively engageable with an eyeglass frame, goggle, or an AR or VR headset, which is positionable to an as-worn position upon a user locating the first surface thereof facing the eyes of a user with the first projecting portion aligned with a first eye of the user and said second projecting portion aligned with a second eye of the user.

2. The corrective lens of claim 1 additionally comprising:

said first sidewall defining a first shape of said first projecting portion, said first shape being substantially rectangular; and said second sidewall defining a second shape of said second projecting portion, said second shape being substantially rectangular.

3. The corrective lens of claim 1 additionally comprising:

said horizontal field of view of corrected vision to the user in a range between 130 and 180 degrees.

4. The corrective lens of claim 2 additionally comprising:

said horizontal field of view of corrected vision to the user in a range between 130 and 180 degrees.

5. The corrective lens of claim 1 additionally comprising:

said bottom of said first sidewall having a first curved section therein;

said bottom of said second sidewall having a second curved section therein; and said first curved section and said second curved section defining an area therebetween for positioning of a nose of the user.

6. The corrective lens of claim 2 additionally comprising:

said bottom of said first sidewall having a first curved section therein;

said bottom of said second sidewall having a second curved section therein; and said first curved section and said second curved section defining an area therebetween for positioning of a nose of the user.

7. The corrective lens of claim 3 additionally comprising:

said bottom of said first sidewall having a first curved section therein;

said bottom of said second sidewall having a second curved section therein; and said first curved section and said second curved section defining an area therebetween for positioning of a nose of the user.

8. The corrective lens of claim 1 additionally comprising:

said first sidewall defining a first shape of said first projecting portion;

said first shape being a first extended rectangular shape where said second end of said first projecting portion positioned closest to said first end of said first lens portion and is wider than said first end of said first projecting portion in said central area of said first lens portion;

said second sidewall defining a second shape of said second projecting portion; and said second shape being a second extended rectangular shape where said second end of said second projecting portion positioned closest to said second end of said first lens portion is wider than said first end of said second projecting portion in said central area of said first lens portion.

9. The corrective lens of claim 2 additionally comprising:

said first sidewall defining a first shape of said first projecting portion;

said first shape being a first extended rectangular shape where said second end of said first projecting portion positioned closest to said first end of said first lens portion and is wider than said first end of said first projecting portion in said central area of said first lens portion;

said second sidewall defining a second shape of said second projecting portion; and said second shape being a second extended rectangular shape where said second end of said second projecting portion positioned closest to said second end of said first lens portion is wider than said first end of said second projecting portion in said central area of said first lens portion.

10. The corrective lens of claim 3 additionally comprising:

said first sidewall defining a first shape of said first projecting portion;

said first shape being a first extended rectangular shape where said second end of said first projecting portion positioned closest to said first end of said first lens portion and is wider than said first end of said first projecting portion in said central area of said first lens portion;

said second sidewall defining a second shape of said second projecting portion; and said second shape being a second extended rectangular shape where said second end of said second projecting portion positioned closest to said second end of said first lens portion is wider than said first end of said second projecting portion in said central area of said first lens portion.

11. A corrective lens for employment in combination with an AR or VR eyewear, said corrective lens comprising:

a first lens portion extending in a curve from a first end thereof to a second end thereof;

a central area of said first lens portion in between said first end and second end of said first lens portion;

said first lens portion having a first surface opposite a second surface on an opposite side from said first surface;

a first projecting portion extending from said first surface of said first lens portion in a first curve, said first projecting portion having a first sidewall thereof extending to a first side surface thereof;

said first side surface of said first projecting portion being processable to form a first curved corrective lens thereon;

a second projecting portion extending from said first surface of said first lens portion, said second projecting portion having a second sidewall thereof extending to a second side surface thereof;

said second projecting portion extending in a second curve from a first side of said second sidewall thereof within said central area of said first lens portion, to a second side of said second sidewall located adjacent said second end of said first lens portion;

said second side surface of said second projecting portion being processable for curved horizontal vision correction therethrough along said second curve;

said second side surface of said second projecting portion processable for vertical vision correction therethrough, between a top of said second sidewall of said second projecting portion and an opposite bottom of said second sidewall of said first projecting portion; and said first lens portion being operatively engageable with an AR or VR headset locating the first surface thereof to an as used position facing the eyes of a user with the first projecting portion aligned with a first eye of the user and said second projecting portion is aligned with a second eye of the user.

12. A corrective lens comprising:

a first lens portion extending in a curve from a first end thereof to a second end thereof;

a central area of said first lens portion in between said first end and second end of said first lens portion;

said first lens portion having a first surface opposite a second surface on an opposite side from said first surface;

a first projecting portion extending from said first surface of said first lens portion, said first projecting portion having a sidewall thereof extending to a first side surface area of said first lens portion;

said first projecting portion extending in a first curve thereof toward said first end of said first lens portion;

said first side surface area being processable to form a first curved corrective lens providing curved vision correction therethrough along said first curve;

a second projecting portion extending from said first surface of said first lens portion, said second projecting portion having a sidewall thereof extending to a second side surface area of said second projecting portion;

said second projecting portion extending in a second curve thereof in a direction away from said first projecting portion and toward said second end of said first lens portion;

said second side surface area being processable to form a second curved corrective lens providing curved vision correction therethrough along said second curve; and wherein said first lens portion is operatively engageable with an eyeglass frame, goggle, or an AR or VR headset, which is positionable to an as-worn position upon a user, locating the first surface thereof facing the eyes of a user with the first side surface area aligned with a first eye of the user and said second side surface area aligned with a second eye of said user to thereby provided curved vision correction to said user.

* * * * *